(12) United States Patent
Branch et al.

(10) Patent No.: US 9,408,771 B2
(45) Date of Patent: Aug. 9, 2016

(54) BLADDER DRIVEN LINEAR CYLINDER AND ASSOCIATED DEVICES DRIVEN THEREBY

(75) Inventors: Thomas P. Branch, Atlanta, GA (US); Thomas Cunningham, Atlanta, GA (US); Edward Dittmar, Marietta, GA (US); Cale Jacobs, Suanee, GA (US)

(73) Assignee: ERMI, INC., Atlanta, GA (US)

( * ) Notice: Subject to any disclaimer, the term of this patent is extended or adjusted under 35 U.S.C. 154(b) by 923 days.

(21) Appl. No.: 13/220,348

(22) Filed: Aug. 29, 2011

(65) Prior Publication Data

US 2012/0053495 A1    Mar. 1, 2012

Related U.S. Application Data

(60) Provisional application No. 61/377,688, filed on Aug. 27, 2010, provisional application No. 61/385,792, filed on Sep. 23, 2010.

(51) Int. Cl.
*A61H 1/02* (2006.01)
*A61F 5/042* (2006.01)

(52) U.S. Cl.
CPC .............. *A61H 1/0274* (2013.01); *A61F 5/042* (2013.01); *A61H 1/02* (2013.01); *A61H 1/0218* (2013.01);

(Continued)

(58) Field of Classification Search
CPC ..... A61H 1/02; A61H 1/0218; A61H 1/0174; A61H 1/0285; A61H 1/0288; A61H 2201/1638; A61H 2201/0103; A61H 2201/123; A61H 2201/1246; A61H 2201/1481; A61H 1/0274; A61F 5/042
USPC ......... 601/5, 9, 23, 24, 26, 27, 33, 34, 35, 40, 601/55, 61, 75, 84, 86, 88, 90, 96, 98, 105, 601/148–152; 602/13
See application file for complete search history.

(56) References Cited

U.S. PATENT DOCUMENTS

| T100,602 I4 | 5/1981 | Roley et al. |
|---|---|---|
| 4,294,141 A | 10/1981 | Miller |
| 4,407,277 A | 10/1983 | Ellison |
| 4,586,495 A | 5/1986 | Petrofsky |

(Continued)

FOREIGN PATENT DOCUMENTS

| CA | 2615171 | 1/2007 |
|---|---|---|
| DE | 36 09 535 | 9/1987 |

(Continued)

OTHER PUBLICATIONS

B.D. Beynnon et al., "The Effect of Functional Knee-Braces On Strain On The Anterior Cruciate Ligament In Vivo," Journal of Bone and Joint Surgery; Boston, US; vol. 74A, No. 9; Oct. 1, 1992; pp. 1298-1312; XP000322579.

(Continued)

*Primary Examiner* — Quang D Thanh
(74) *Attorney, Agent, or Firm* — Moore & Van Allen, PLLC; Patrick B. Horne

(57) ABSTRACT

An apparatus for manipulating the joint of a patient is provided. The apparatus comprises an actuator and a linkage. The actuator itself comprises: 1) a cylinder portion defining an interior cavity; and 2) an inflatable bladder member at least partially inside the cavity of the cylinder portion. The linkage is operatively positioned intermediate the actuator and the joint of the patient, the linkage configured to be activated and to flex the joint upon inflation of the bladder. A piston portion may also be provided and configured to move relative to cylinder portion within the cavity in response to inflation of the bladder. A patient connection and manipulation device may also be provided within the apparatus and configured to be attached relative to the patient, attached intermediate the linkage and the patient, and configured to at least partially assist with treatment upon activation of the linkage.

33 Claims, 30 Drawing Sheets

(52) U.S. Cl.
CPC ............ *A61H 1/0285* (2013.01); *A61H 1/0288* (2013.01); *A61H 2201/0103* (2013.01); *A61H 2201/123* (2013.01); *A61H 2201/1246* (2013.01); *A61H 2201/1481* (2013.01); *A61H 2201/1638* (2013.01)

(56) References Cited

U.S. PATENT DOCUMENTS

| | | | |
|---|---|---|---|
| 4,650,183 | A | 3/1987 | McIntyre |
| 4,727,860 | A | 3/1988 | McIntyre |
| 4,733,859 | A | 3/1988 | Kock et al. |
| 4,771,548 | A | 9/1988 | Donnery |
| 4,782,831 | A | 11/1988 | Gallant |
| 4,823,807 | A | 4/1989 | Russell et al. |
| 4,825,852 | A | 5/1989 | Genovese et al. |
| 4,834,073 | A | 5/1989 | Bledsoe et al. |
| 4,909,262 | A | 3/1990 | Halpern et al. |
| 4,930,497 | A | 6/1990 | Saringer |
| 5,027,799 | A | 7/1991 | Laico et al. |
| 5,056,535 | A | 10/1991 | Bonnell |
| 5,211,161 | A | 5/1993 | Stef |
| 5,228,432 | A | 7/1993 | Kaiser et al. |
| 5,335,674 | A | 8/1994 | Siegler |
| 5,362,298 | A * | 11/1994 | Brown et al. ................... 601/40 |
| 5,382,225 | A | 1/1995 | Sutcliffe |
| 5,399,147 | A | 3/1995 | Kaiser |
| 5,402,800 | A | 4/1995 | Hollis |
| 5,435,321 | A | 7/1995 | McMillen et al. |
| 5,645,079 | A | 7/1997 | Zahiri et al. |
| 4,278,860 | A | 3/1998 | McIntyre |
| 6,599,255 | B2 | 7/2003 | Zhang |
| 6,669,660 | B2 | 12/2003 | Branch |
| 6,821,231 | B1 | 11/2004 | Hall |
| 6,872,186 | B2 | 3/2005 | Branch et al. |
| 7,041,069 | B2 | 5/2006 | West |
| 7,479,121 | B2 | 1/2009 | Branch |
| 7,547,289 | B2 | 6/2009 | Branch |
| 7,628,766 | B1 | 12/2009 | Kazerooni et al. |
| 7,665,167 | B2 | 2/2010 | Branch et al. |
| 7,753,862 | B2 | 7/2010 | Branch et al. |
| 7,854,685 | B2 | 12/2010 | Cole et al. |
| 7,951,097 | B2 | 5/2011 | Schaeffer |
| 7,985,227 | B2 | 7/2011 | Branch et al. |
| 2004/0260208 | A1 | 12/2004 | Laprade et al. |
| 2005/0222573 | A1 | 10/2005 | Branch et al. |
| 2006/0064048 | A1 | 3/2006 | Stano |
| 2006/0097557 | A1 | 5/2006 | Tholkes et al. |
| 2007/0055176 | A1 | 3/2007 | Branch et al. |
| 2007/0123997 | A1 | 5/2007 | Herr et al. |
| 2007/0129653 | A1* | 6/2007 | Sugar et al. ................... 601/5 |
| 2009/0124936 | A1 | 5/2009 | Branch et al. |
| 2009/0264797 | A1 | 10/2009 | Mayr |
| 2010/0179605 | A1 | 7/2010 | Branch et al. |
| 2012/0046540 | A1 | 2/2012 | Branch et al. |
| 2012/0085353 | A1 | 4/2012 | Siston |

FOREIGN PATENT DOCUMENTS

| | | |
|---|---|---|
| DE | 39 25 014 | 1/1991 |
| EP | 0 204 639 | 12/1986 |
| EP | 0293372 | 6/1991 |
| EP | 1 219 240 | 7/2002 |
| WO | WO 88/04536 A1 | 6/1988 |
| WO | WO 8804536 | 6/1988 |
| WO | WO 9302621 | 2/1993 |
| WO | WO 02/096274 | 12/2002 |
| WO | WO 2007/009063 | 1/2007 |
| WO | WO 2009/064367 | 5/2009 |
| WO | WO 2012021726 A1 | 2/2012 |

OTHER PUBLICATIONS

Daniel, "MEDmetric® Knee Ligament Arthrometer ModelsKT1000™ and KT2000™," Reference, Maintenance and User guide for the Knee Ligament Arthrometer®, 1$^{st}$ Ed., May 1993, 51 pp. San Diego, CA.

International Search Report for International Application No. PCT/US2006/027376 filed Apr. 19, 2007.

International Search Report from corresponding International Application No. PCT/US2008/012578.

Invitation to Pay Additional Fees and, where Applicable, Protest Fee Search Report for International Application No. PCT/US2008/012578.

Li-Wun Zhang et al., "Dynamic and Static Properties of The Human Knee Joint in Axial Rotation," Engineering in Medicine and Biology Society, 1997, Proceedings of the 19th Annual International Conference of the IEEE Chicago, IL, USA Oct. 30-Nov. 2, 1997; Piscataway, NJ, USA, IEEE, US; vol. 4; Oct. 30, 1997; pp. 1738-1741; XP010325504.

Markolf, K. L., et al., "In vivo knee stability. A quantitative assessment using an instrumented clinical testing apparatus," Journal of Bone and Joint Surgery, American Volume Jul. 1978, vol. 60, No. 5, Jul. 1978, XP002515912, ISSN: 0021-9355, p. 664-p. 674.

Medmetric Corporation, "In These Times of Managed Care, Measured Outcomes are Crucial," found at http://web.archive.org/web120040610111553/http://medmetric.com (1 page).

Medmetric Corporation, "KT1000/S;" found at http://web.archive.org/web/20040628060104/www.kt1000.com/kts.htm (2 pages).

Medmetric Corporation, "KT2000," found at http://web.archive.org/web/20040618192953/www.kt1000.com/kts.htm (2 pages).

Notice of Allowance dated Mar. 9, 2010, U.S. Appl. No. 11/457,443, filed Jul. 13, 2006.

Office Action dated Aug. 6, 2009, U.S. Appl. No. 11/457,443, filed Jul. 13, 2006.

Roley et al., "T100,602—Apparatus for Measuring Angles," United States Defensive Publication, May 5, 1981; 5 pages.

S.C. Shoemaker et al., "In-Vivo Rotatory Knee Stability Ligamentous and Muscular Contributions," Journal of Bone and Joint Surgery; Boston, US; vol. 64, No. 2; 1982; pp. 208-216; XP008050394.

Shino, K. et al., "Measurement of anterior instability of the knee. A new apparatus for clinical testing," The Journal of Bone and Joint Surgery, British Volume, Aug. 1987, vol. 69, No. 4, Aug. 1987, XP002515908; ISSN: 0301-620X, p. 608-p. 613.

Shultz Sandra, J., et al., "Measurement of varus-valgus and internal-external rotational knee laxities in vivo—Part I: assessment of measurement reliability and bilateral asymmetry," Journal of Orthopaedic Research: Official Publication of the Orthopaedic Research Society, Aug. 2007, vol. 25, No. 8, Aug. 2007, XP002515908, ISSN: 0736-0266, p. 981-p. 988.

Uh B.S., et al., "A new device to measure knee laxity during weightbearing and non-weightbearing conditions," Journal of Orthopaedic Research: Official Publication of the Orthopaedic Research Society Nov. 2001, vol. 19, No. 6, Nov. 2001, XP002515911; ISSN: 0736-0266, p. 1185-p. 1191.

Van Der Esch, M. et al., "Reproducibility of instrumented knee joint laxity measurement in healthy subjects," Rheumatology (Oxford, England) May 2006, vol. 45, No. 5, May 2006, pp. 595-599, XP002515910; ISSN: 1462-0324.

International Search Report and Written Opinion of the International Searching Authority dated Nov. 17, 2011, for Application No. PCT/US2011/047696.

Branch, et al. "Instrumented Examination of Anterior Cruciate Ligament Injuries: Minimizing Flaws of the Manual Clinical Examination," Arthroscopy, vol. 26, No. 7, Jul. 2010, pp. 997-1004.

International Preliminary Examining Authority, Written Opinion for International Application No. PCT/US2011/047696, mailed Aug. 3, 2012, 8 pages, European Patent Office, The Netherlands.

United States Patent and Trademark Office, Office Action for U.S. Appl. No. 12/797,324, dated Oct. 1, 2012, 9 pages, USA.

Office Action dated Feb. 7, 2012 in U.S. Appl. No. 12/267,109, filed Nov. 7, 2008.

Office Action dated Dec. 9, 2011 in U.S. Appl. No. 12/797,324, filed Jun. 9, 2010.

(56) References Cited

OTHER PUBLICATIONS

European Patent Office, Office Action dated Apr. 4, 2012, for Application No. EP06787304.2.
United States Patent and Trademark Office, Office Action for U.S. Appl. No. 13/209,380, Jun. 4, 2013, 29 pages, USA.
Office Action dated Dec. 9, 2011 for U.S. Appl. No. 12/797,324, filed Jun. 9, 2010.
International Searching Authority, ISR and Written Opinion for International Appn No. PCT/US20121048377, mailed Jan. 4, 2013, 20 pages, EPO, The Netherlands.
United States Patent and Trademark Office, Office Action for U.S. Appl. No. 12/267,109, dated Mar. 13, 2013, 28 pages, USA.
International Searching Authority, ISR and Written Opinion for International Appn No. PCT/US2013/060229, mailed Dec. 5, 2013, 12 pages, EPO, The Netherlands.

* cited by examiner

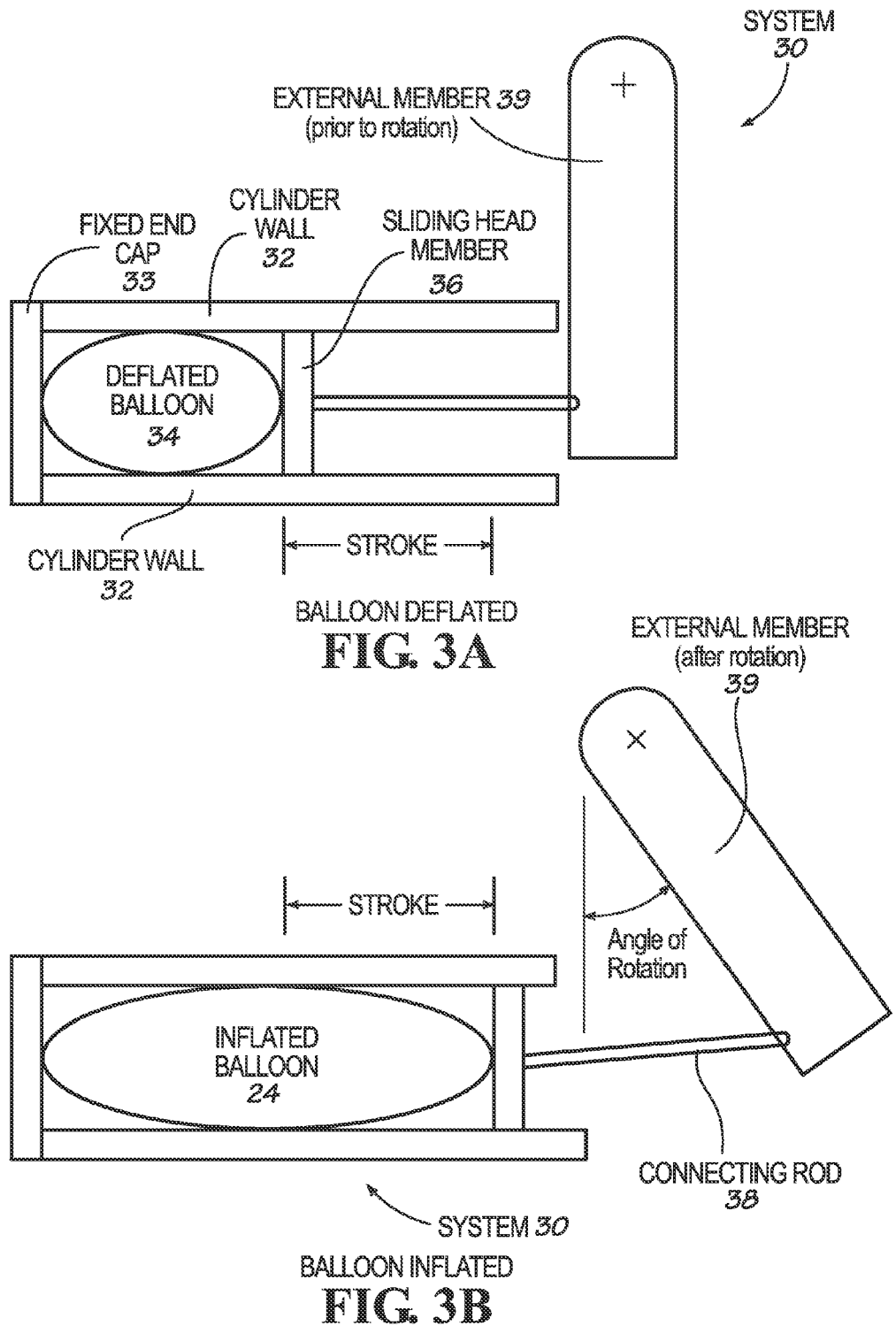

Tension string with one end fixed to the external member, passing over the sliding head member, with the other end fixed to the cylinder Tension string passing over the sliding head member, with both ends fixed to the external member

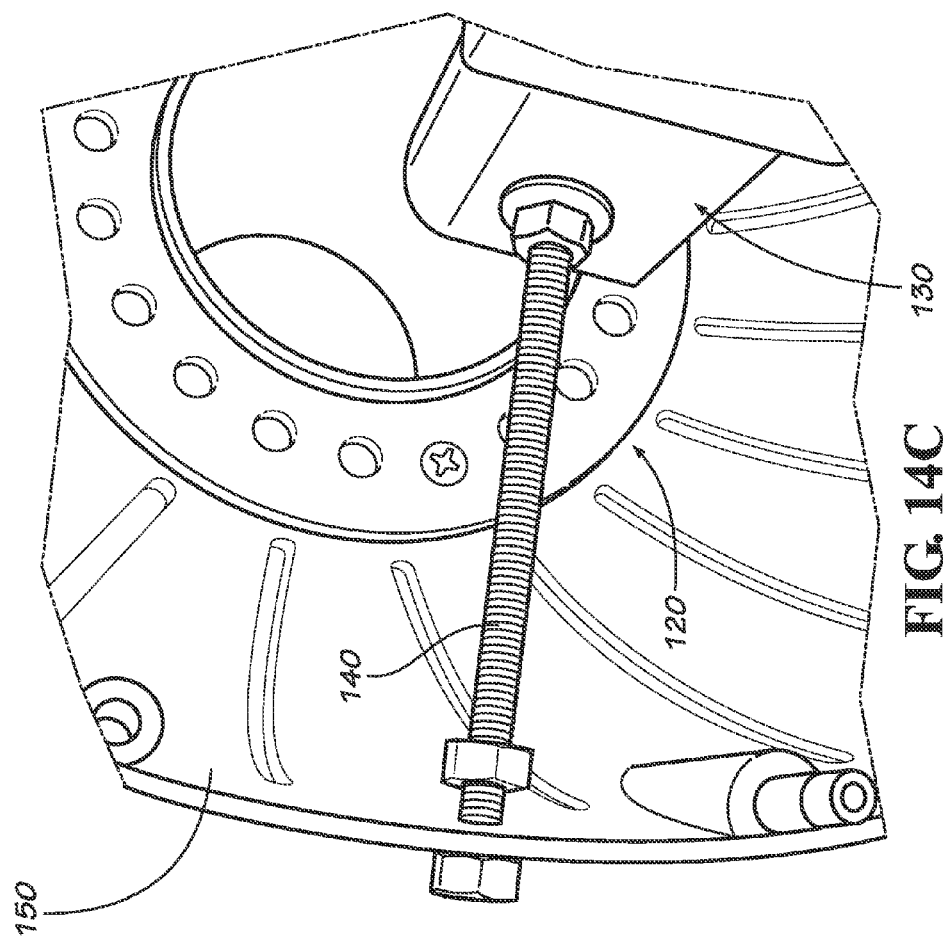

WRIST EXTENSION

WRIST FLEXION

WRIST EXTENSION

WRIST FLEXION

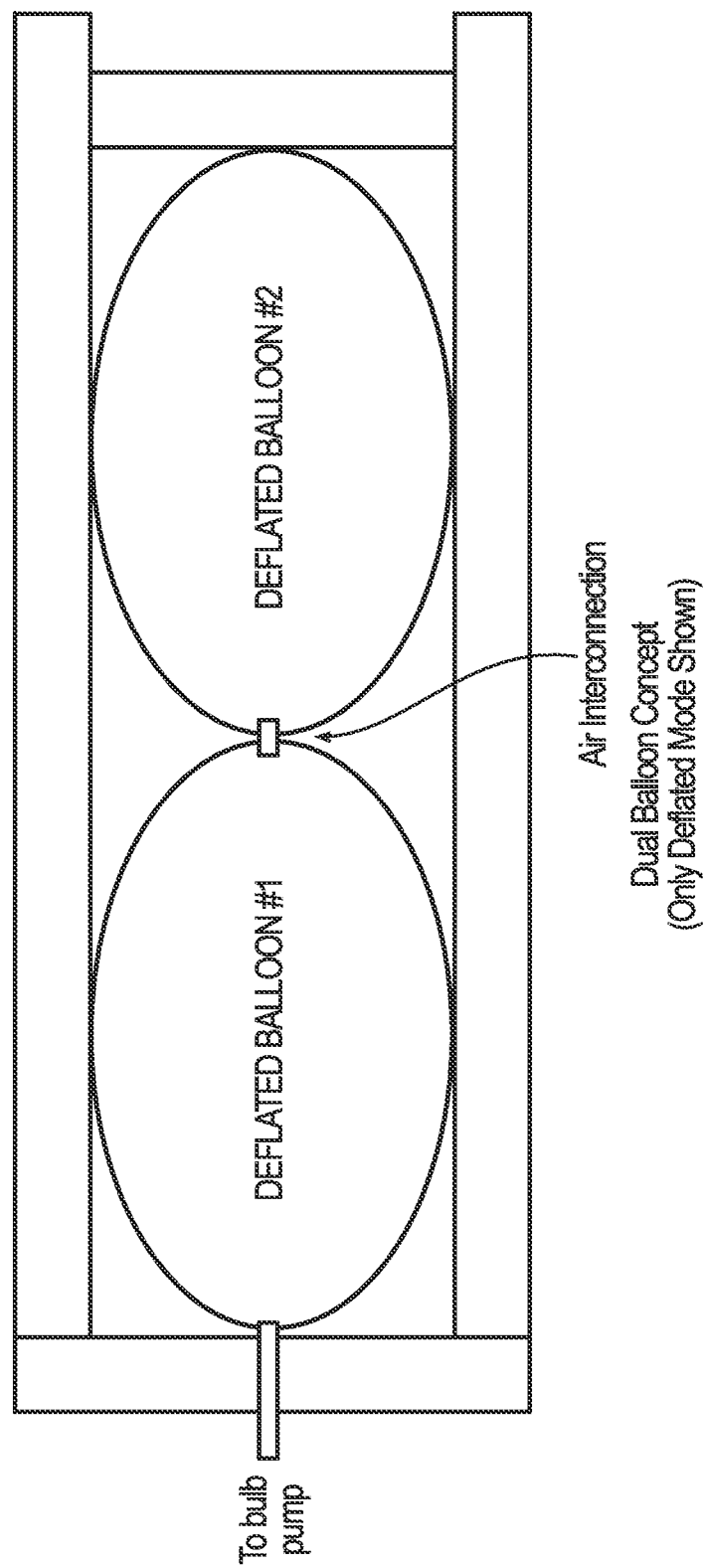

BLADDER DRIVEN LINEAR CYLINDER AND ASSOCIATED DEVICES DRIVEN THEREBY

CROSS-REFERENCE TO RELATED APPLICATIONS

This application claims priority to and the benefit of U.S. Provisional Application No. 61/377,688, filed Aug. 27, 2010, entitled "Robotic Knee Testing Device, Subjective Patient Input Device, Bladder Driven Linear Actuator, and Methods for Using the Same," and U.S. Provisional Application No. 61/385,792, filed Sep. 23, 2010, entitled "Bladder Driven Linear Cylinder and Associated Devices Driven Thereby," both of which are incorporated herein in their entirety.

BACKGROUND

1. Field of Invention

The present invention relates generally to an orthotic apparatus and to mechanical devices for use with the same that together assist with enabling the full normal motion of a joint as an alternative to surgical manipulation.

2. Description of Related Art

The number one complication of a joint injury is loss of motion. The loss of motion is often due to an excess production of fibrous tissue within the joint called arthrofibrosis. Arthrofibrosis is both a mechanical and a biological process which results in loss of motion of a joint.

Synovial cells make up the lining of a joint. These cells are the source of the problem called arthrofibrosis. The synovial cells transform themselves into fibroblasts upon exposure to cytokines and growth factors produced by damaged vascular endothelium. Sudden increases in range of motion produced by intermittent vigorous physical therapy or intra-operative manipulation cause bleeding within the joint further exposing the synovial cells to the cytokines and growth factors which cause arthrofibrosis.

The current methods for gaining range of motion in joints with early or late arthrofibrosis include vigorous physical therapy, specialized splints, continuous passive motion machines and surgical manipulation under anesthesia. Unfortunately, vigorous physical therapy and surgical manipulation under anesthesia have a high failure rate associated with peri-articular bleeding and the resultant progression of arthrofibrosis. Continuous passive motion machines are not effective as they spend most of the time in the middle range of motion of the joint and not focused on stretching at end range of motion.

The current specialized splints include serial casting, Dynasplint and the Joint Active System, on which the invention will provide personal opinions. All of these splints enclose the limb segment proximal and distal to the joint that needs to be stretched. Furthermore, the Dynasplint allows for only a low load stretching process. The Joint Active Systems devices allow for higher loads to be placed at the joint but at the expense of increased pressure at the limb segments proximal and distal to the joint. The loads used by the Joint Active Systems are low in intensity. Serial casting splints are not removable by the patient and have limited adjustability to change the load placed at the joint. Due to the splint design of these devices energy is trapped within the structure of the splints during the stretching process. As a result there is an unpredictable variation in load seen by the joint during the stretching process. This 'unpredictability' creates a sense of unease in the patient using the device to gain range of motion. None of these devices produce a load high enough to assure that for every degree the device moves the joint moves the same amount. Finally, none of these devices allow for an instantaneous or quick release of the load applied to the joint.

There is a need to produce an orthotic device for the treatment of arthrofibrosis, which can stretch the joint into full normal end range of motion in a predictable, consistent and reliable fashion. This device should be rigid enough to not allow the storage of energy within its structure. Furthermore, it should be able to produce a load at the joint high enough to assure that for every degree the device moves the joint moves the same amount. Finally, this orthotic device should allow for instantaneous or quick release of the load applied to the joint.

SUMMARY

Generally described, the present invention to provide apparatuses and methods for evaluating the performance of joints and their associated elements.

In accordance with the purposes of the various embodiments of the present invention as described herein, an apparatus is provided that comprises an actuator and a linkage. The actuator itself comprises: 1) an actuator portion defining an interior cavity; and 2) an inflatable bladder member at least partially inside the cavity of the cylinder portion. The inflatable bladder includes a movable inflatable bladder portion that is configured to move in response to inflation of the bladder. The linkage is operatively positioned intermediate the movable inflatable bladder portion and an area of a patient needing treatment and further configured to be activated and to impose treatment upon inflation of the bladder.

In accordance with an additional aspect of the present invention, an apparatus is provided that comprises an actuator, a linkage, and a patient connection and manipulation device. The actuator itself comprises: 1) an actuator portion defining an interior cavity; and 2) an inflatable bladder member at least partially inside the cavity of the cylinder portion. The inflatable bladder includes a movable inflatable bladder portion that is configured to move in response to inflation of the bladder. The linkage is operatively positioned intermediate the movable inflatable bladder portion and an area of a patient needing treatment and further configured to be activated and to impose treatment upon inflation of the bladder. The patient connection and manipulation device is configured to be attached relative to the patient, attached intermediate the linkage and the patient, and configured to at least partially assist with treatment upon activation of the linkage.

In accordance with an additional aspect of the present invention, a joint manipulation device for manipulating the joint of a patient, the patient having two bones connected at the joint, is provided. The joint manipulation device comprises an actuator and a linkage. The actuator itself comprises: 1) a cylinder portion defining an interior cavity; 2) a piston portion configured to move relative to cylinder portion within the cavity; and 3) an inflatable bladder member at least partially inside the cavity of the cylinder portion, the actuator configured such that inflation of the bladder causes the piston portion to move relative to cylinder portion. The linkage is operatively positioned intermediate the actuator and the joint of the patient, the linkage configured to be activated and to flex the joint upon inflation of the bladder.

In accordance with an additional aspect of the present invention, a joint manipulation device for manipulating the joint of a patient, the patient having two bones connected at the joint, is provided. The joint manipulation device comprises an actuator and a linkage. The actuator itself comprises: 1) a cylinder portion defining an interior cavity; 2) a piston portion configured to move relative to cylinder portion within the cavity; and 3) an inflatable bladder member at least partially inside the cavity of the cylinder portion, the actuator configured such that inflation of the bladder causes the piston portion to move relative to cylinder portion. The linkage is operatively positioned intermediate the actuator and the joint of the patient, the linkage configured to be activated and to flex the joint upon inflation of the bladder.

In accordance with an additional aspect of the present invention, a joint manipulation device for manipulating the joint of a patient, the patient having two bones connected at the joint, is provided. The joint manipulation device comprises an actuator and a linkage. The actuator itself comprises: 1) a cylinder portion defining an interior cavity; 2) a piston portion configured to move linearly relative to cylinder portion within the interior cavity; and 3) an inflatable bladder member at least partially inside the cavity of the cylinder portion, the actuator configured such that inflation of the bladder causes the piston portion to move linearly relative to cylinder portion within the interior cavity. The linkage is operatively positioned intermediate the actuator and the joint of the patient, the linkage configured to be activated and to flex the joint upon inflation of the bladder.

In accordance with an additional aspect of the present invention, a joint manipulation device for manipulating the joint of a patient, the patient having two bones connected at the joint, is provided. The joint manipulation device comprises an actuator, a linkage, and a patient connection and manipulation device. The actuator comprises: 1) a cylinder portion defining an interior cavity; 2) a piston portion configured to move linearly relative to cylinder portion within the interior cavity; and 3) an inflatable bladder member at least partially inside the cavity of the cylinder portion, the actuator configured such that inflation of the bladder causes the piston portion to move linearly relative to cylinder portion within the interior cavity. The linkage is operatively positioned intermediate the actuator and the joint of the patient, the linkage configured to be activated and to flex the joint upon inflation of the bladder. The patient connection and manipulation device is configured to be attached relative to the patient, attached intermediate the linkage and the patient, and configured to at least partially assist flexion of the joint of the patient upon activation of the linkage.

In accordance with an additional aspect of the present invention, a joint manipulation device for manipulating the joint of a patient, the patient having two bones connected at the joint, is provided. The joint manipulation device comprises an actuator, a linkage, and a patient connection and manipulation device. The actuator comprises: 1) an actuator portion defining an interior cavity; 2) an inflatable bladder member at least partially inside the cavity of the cylinder portion, the inflatable bladder including a movable inflatable bladder portion, the actuator configured such that inflation of the bladder causes the movable inflatable bladder portion to move. The linkage is operatively positioned intermediate the movable inflatable bladder portion and the joint of the patient, the linkage configured to be activated and to flex the joint upon inflation of the bladder. The patient connection and manipulation device is configured to be attached relative to the patient, attached intermediate the linkage and the patient, and configured to at least partially assist flexion of the joint of the patient upon activation of the linkage.

Other aspects, features, and advantages of the present invention will become apparent upon reading the following detailed description of the preferred embodiment of the invention when taken in conjunction with the drawing and the appended claims.

BRIEF DESCRIPTION OF THE DRAWINGS

Figure 1A:
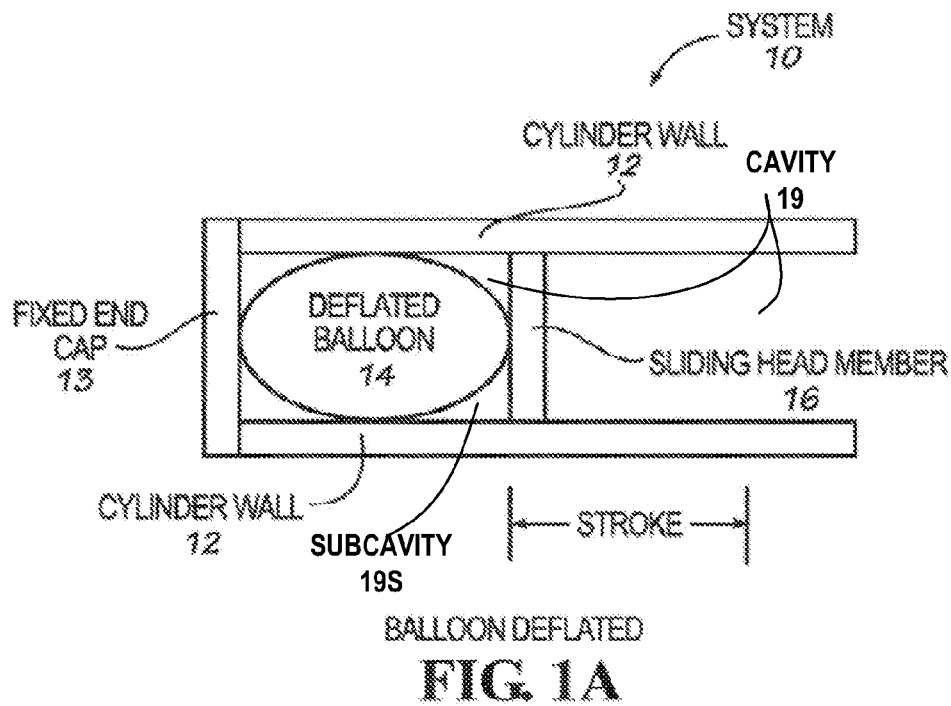
Figure 1B:
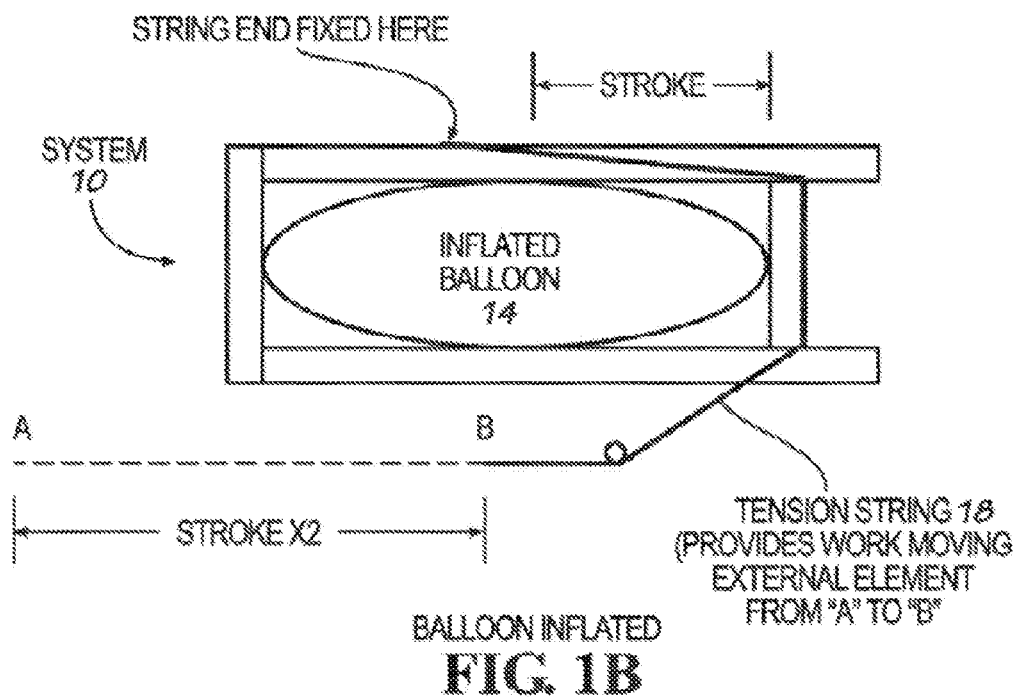

Having thus described the invention in general terms, reference will now be made to the accompanying drawings, which are not necessarily drawn to scale, and wherein:

FIGS. 1A-1B show a bladder driven linear actuator system 10 including a linear cylinder driven by an interior inflatable balloon 14.

Figure 2A:
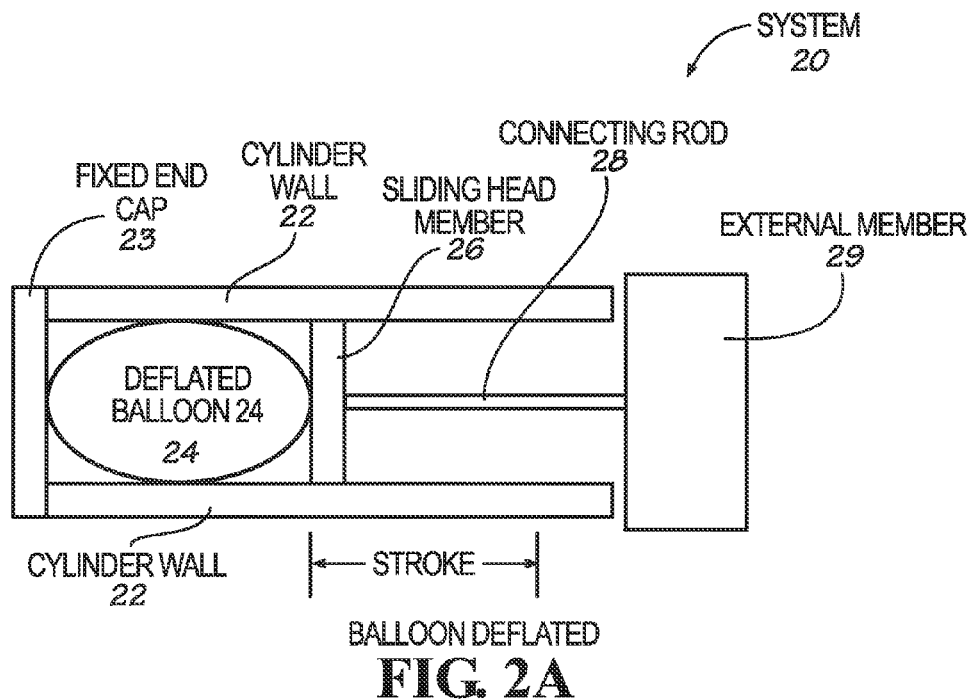
Figure 2B:
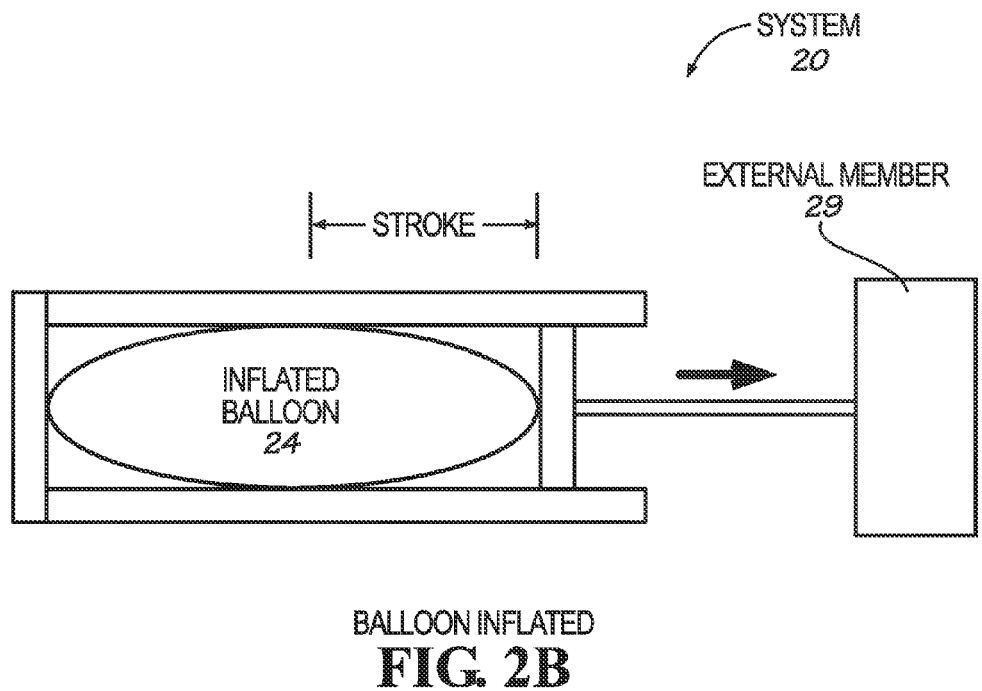

FIGS. 2A-2B show a bladder driven linear actuator system 20 including a linear cylinder driven by an interior inflatable balloon 24.

FIGS. 3A-3B show a bladder driven linear actuator system 30 including a linear cylinder driven by an interior inflatable balloon 34.

Figure 4:
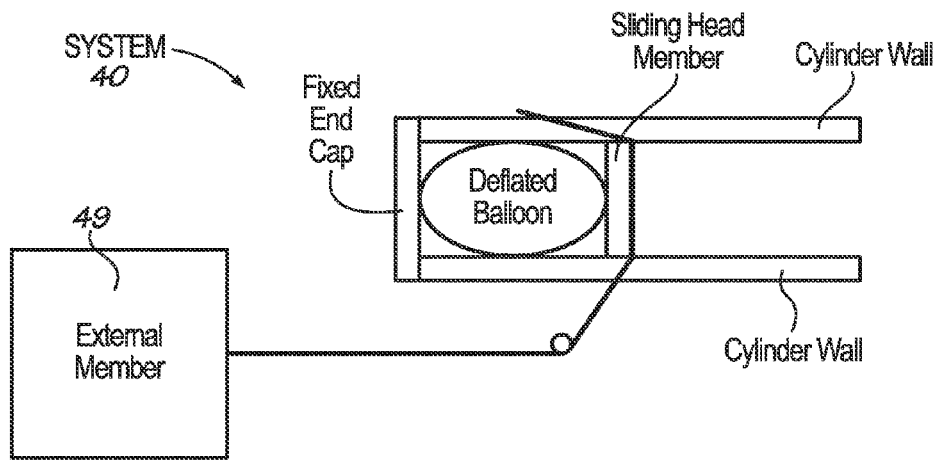

FIG. 4 shows a bladder driven linear actuator system 40 including a linear cylinder driven by an interior inflatable balloon, such that an external member 49 can be moved via string tension.

Figure 5:
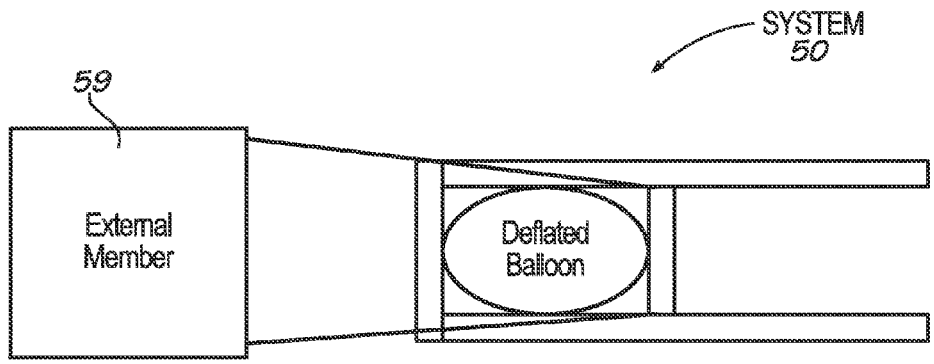

FIG. 5 shows a bladder driven linear actuator system 50 including a linear cylinder driven by an interior inflatable balloon, such that an external member 49 can be moved via string tension. In this embodiment, both ends of the tension string are attached to the external member 59.

Figure 6A:
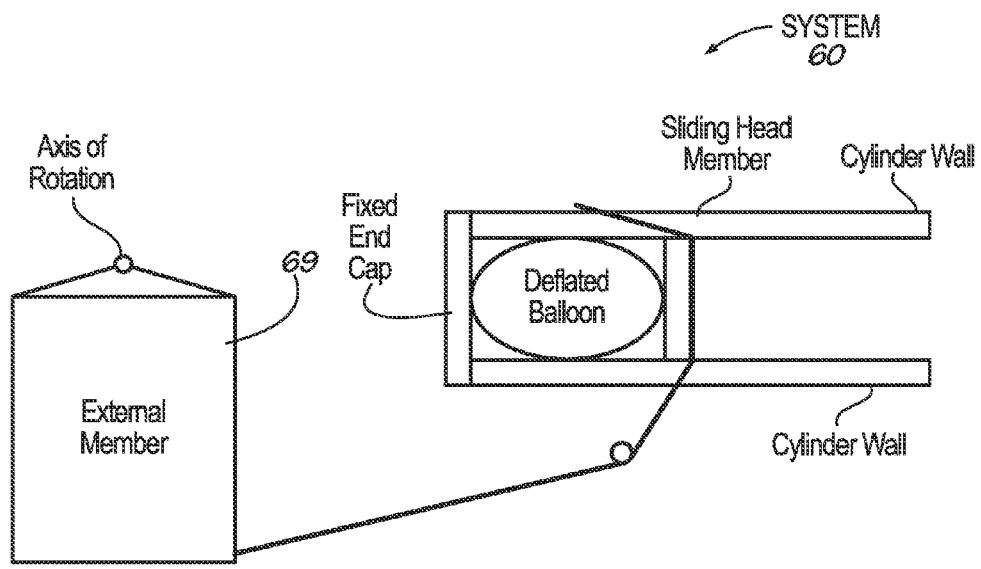
Figure 6B:
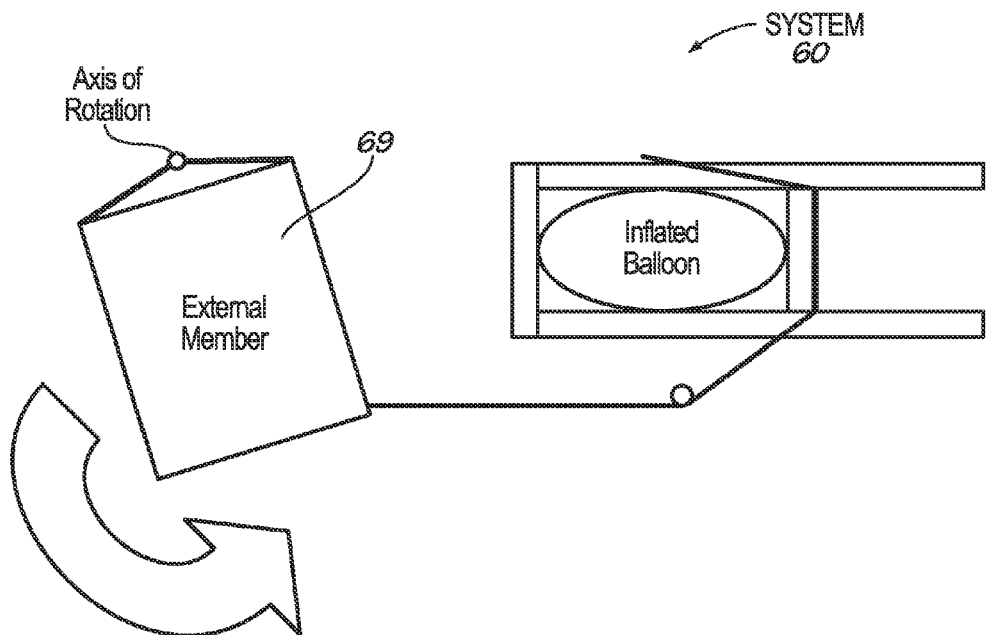

FIGS. 6A-6B show a bladder driven linear actuator system 60 including a linear cylinder driven by an interior inflatable balloon such that an external member can be moved about an axis of rotation.

Figure 7:
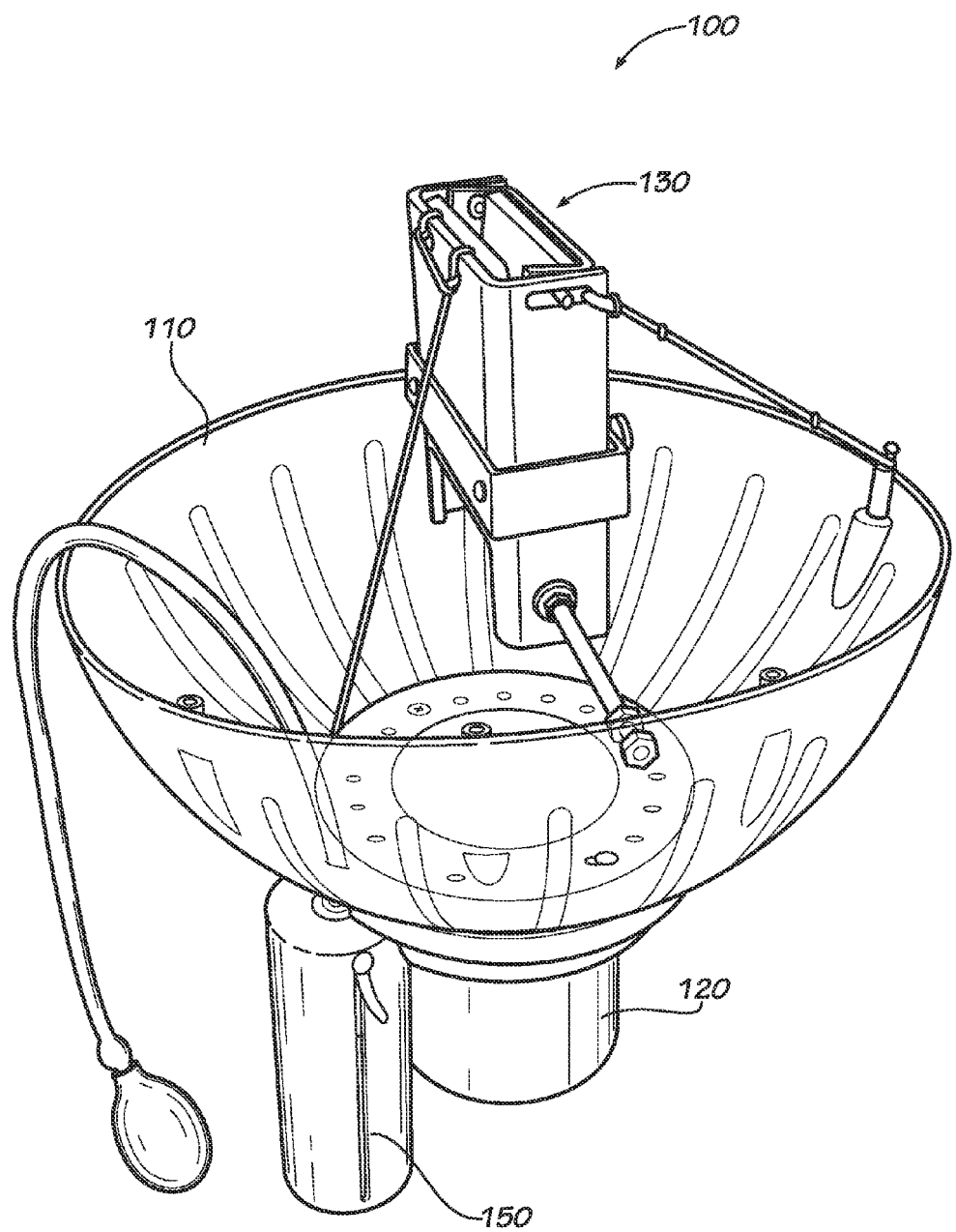

FIG. 7 shows therapy device 100 according to one embodiment of the invention, including a bladder driven linear actuator system 150 is similar to the bladder driven linear actuator system 10 described above. Note that only half of the globe 110 is shown for purposes of illustration.

Figure 8:
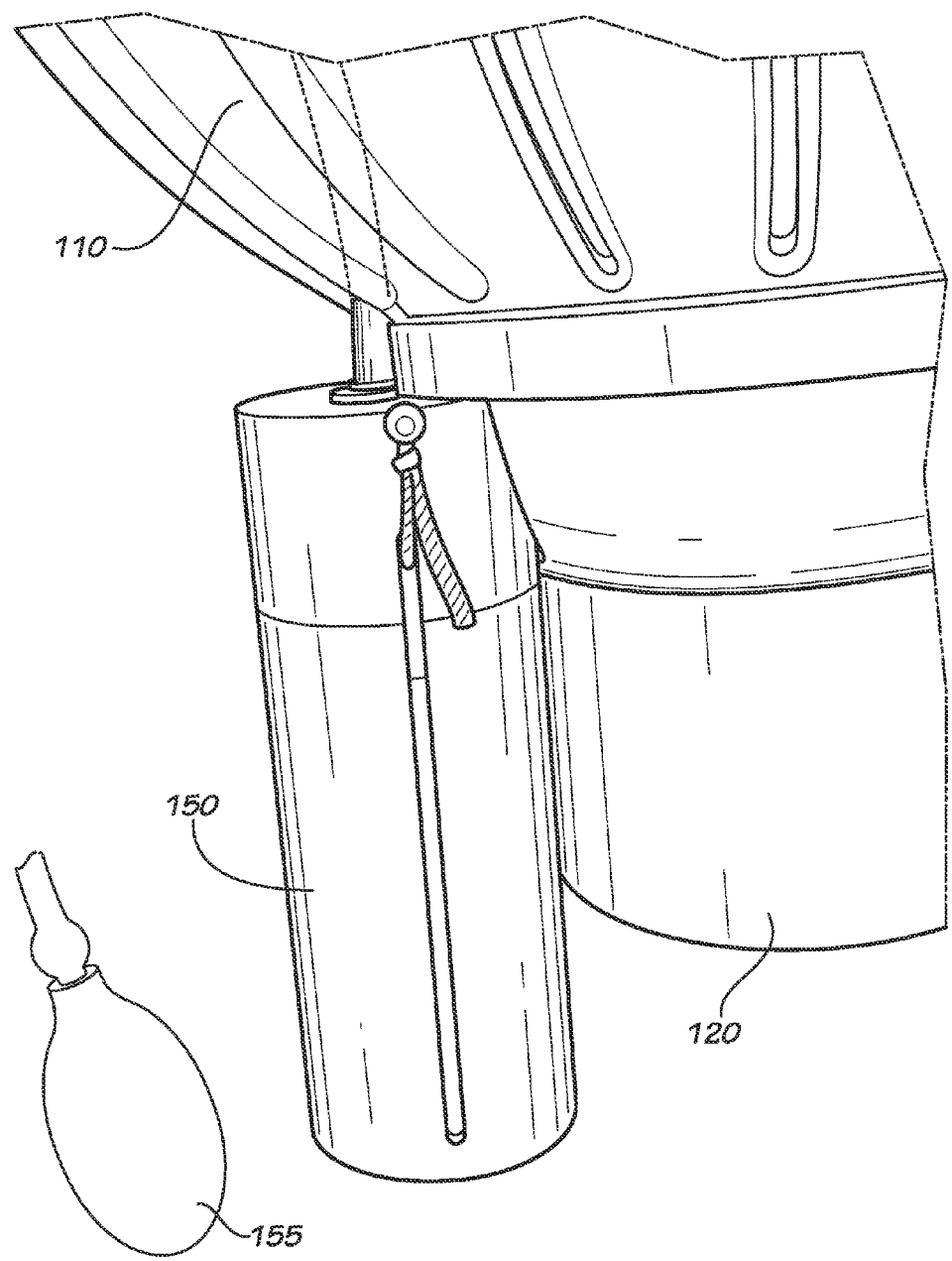

FIG. 8 shows a portion of the therapy device 100, showing the bladder driven actuator system 150 in more detail. Note that only half of the globe 110 is shown for purposes of illustration.

Figure 9:
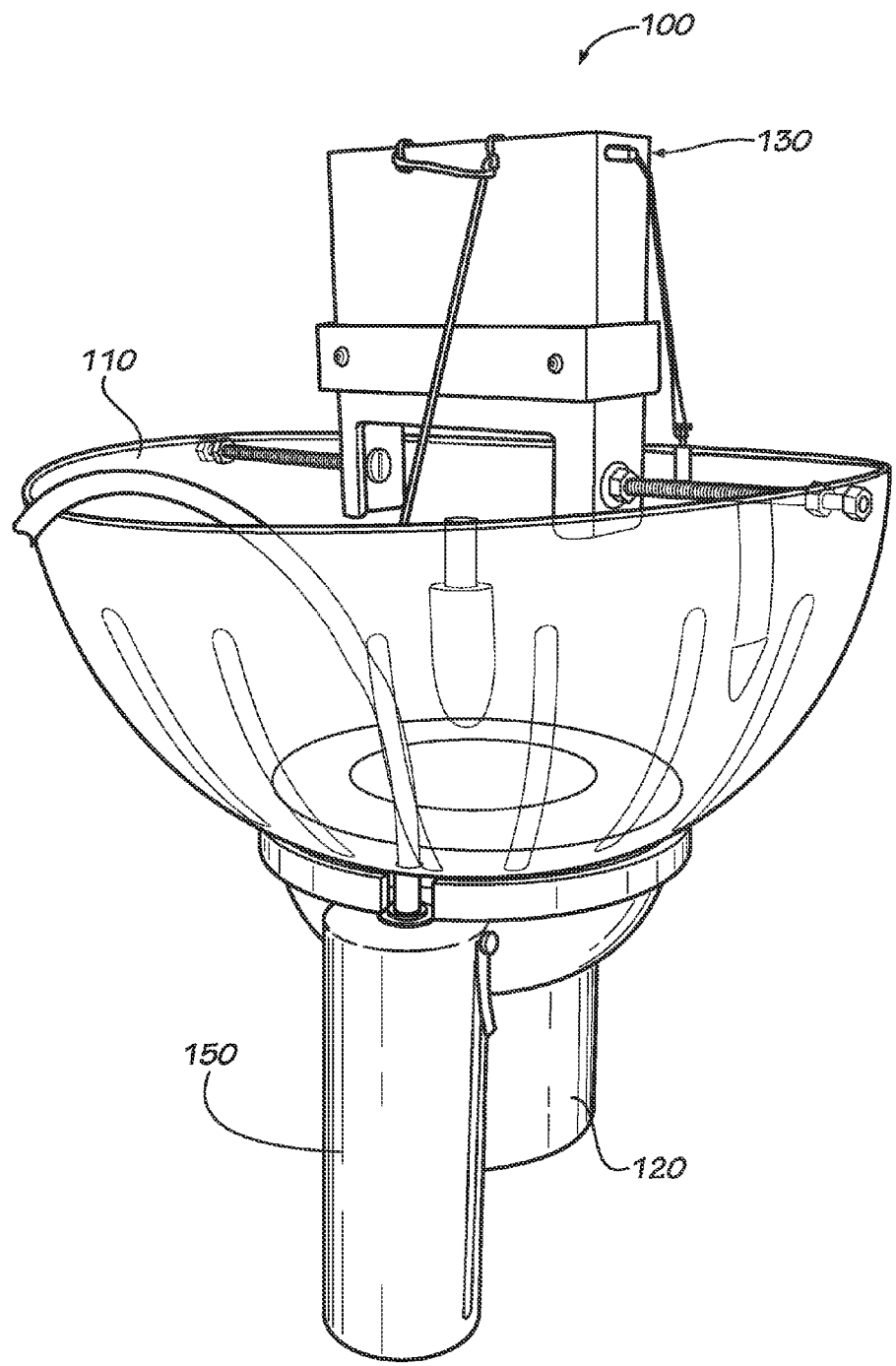

FIG. 9 shows the therapy device 100 from another point of view. Note that only half of the globe 110 is shown for purposes of illustration.

Figure 10:
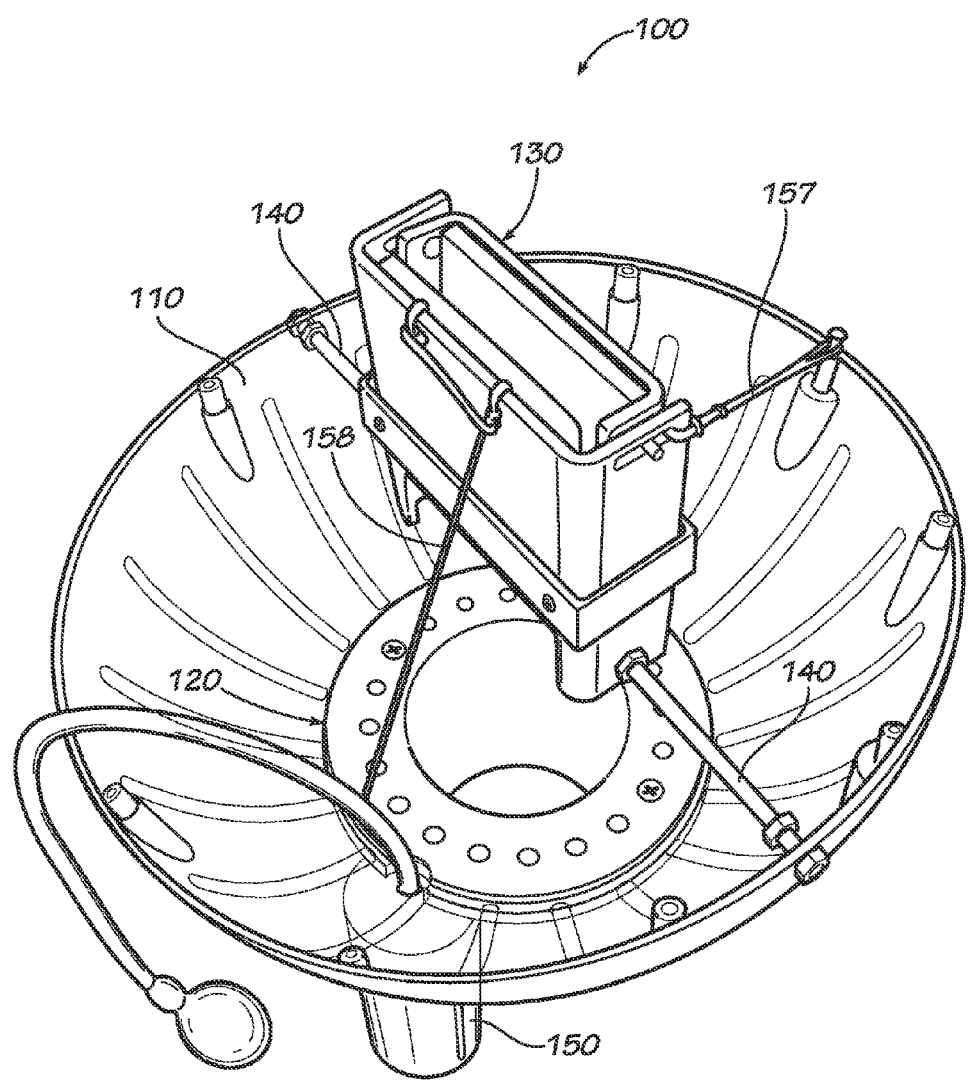

FIG. 10 shows the therapy device 100 from another point of view. Note that only half of the globe 110 is shown for purposes of illustration. As may be seen, the pivot rod 140 is in two segments; each segment has one end attached to the globe and one end attached relative to the body of the hand capturing member 130. Each of the segments is fixed to one of the globe 110 or the body of the hand capturing member 130, and rotatably mounted to the other of the globe 110 or the body of the hand capturing member 130, such that the hand capturing member 130 can pivot (or rotate) relative to the globe 110 about an axis that coincides with the coinciding longitudinal axes of the two segments.

Figure 11:
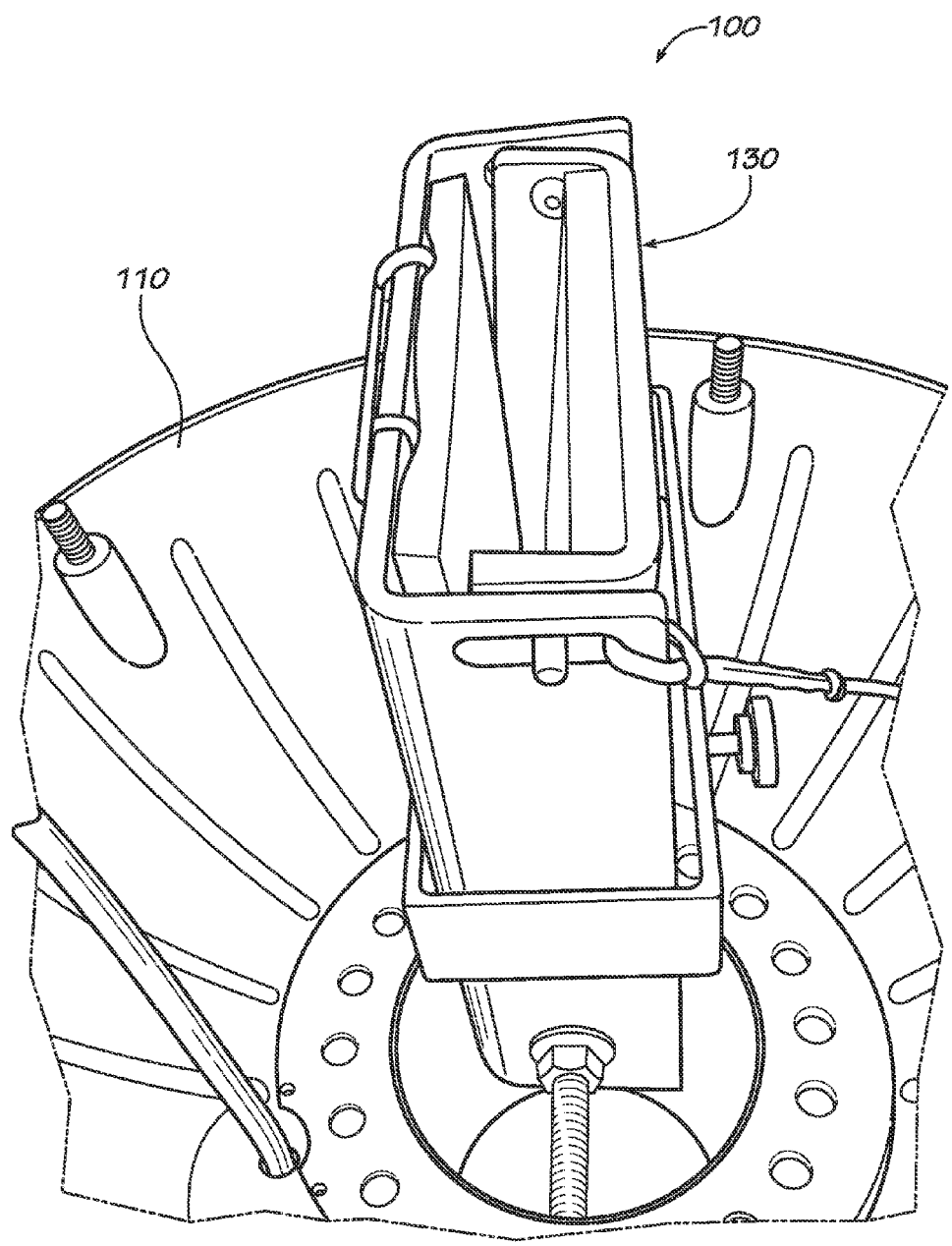

FIG. 11 shows the therapy device 100 from another point of view. Note that only half of the globe 110 is shown for purposes of illustration.

Figure 12:
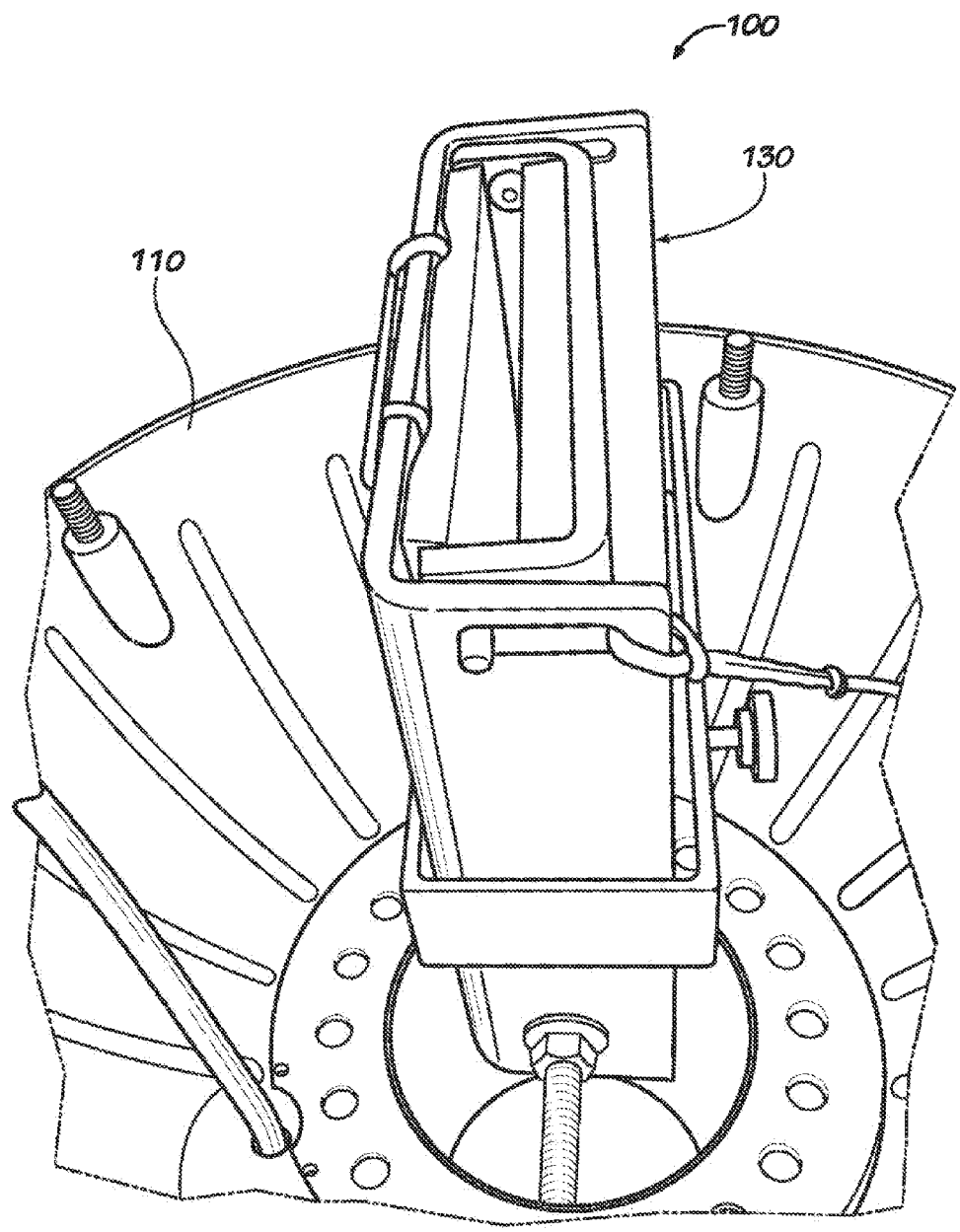

FIG. 12 shows another view similar to FIG. 11, except that the hand capturing member 130 is more open in this figure than in FIG. 11.

Figure 13A:
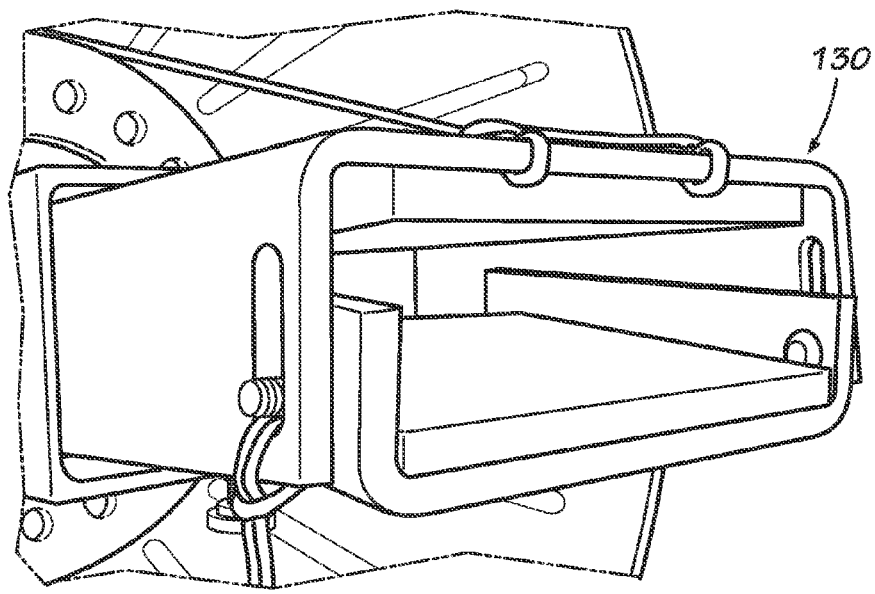
Figure 13B:
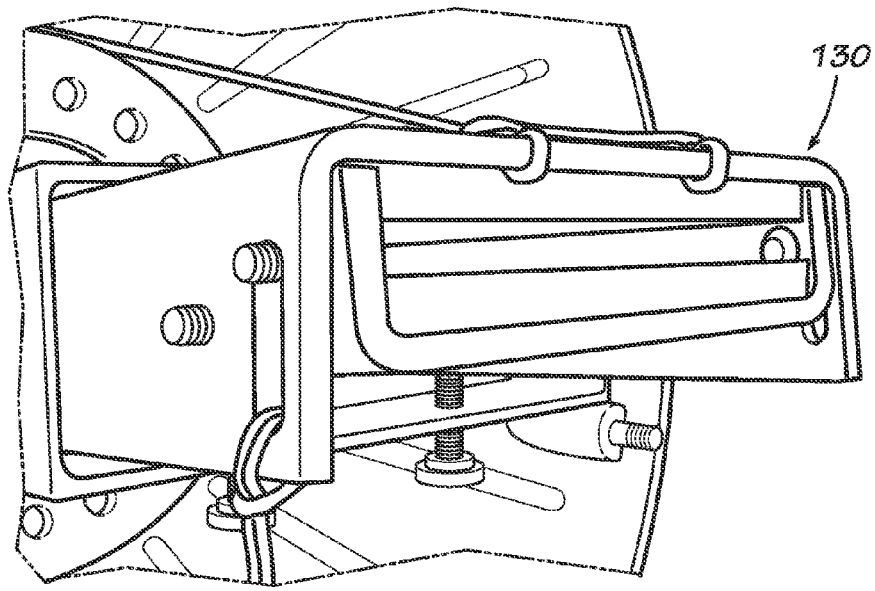

FIGS. 13A-13B show more and less open views of the hand capturing member, respectively.

Figure 14A:
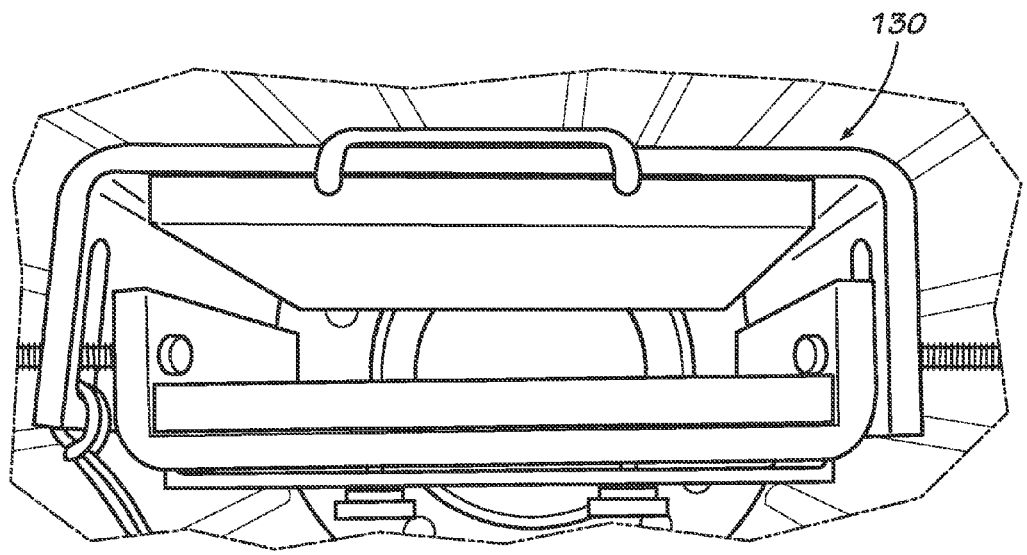
Figure 14B:
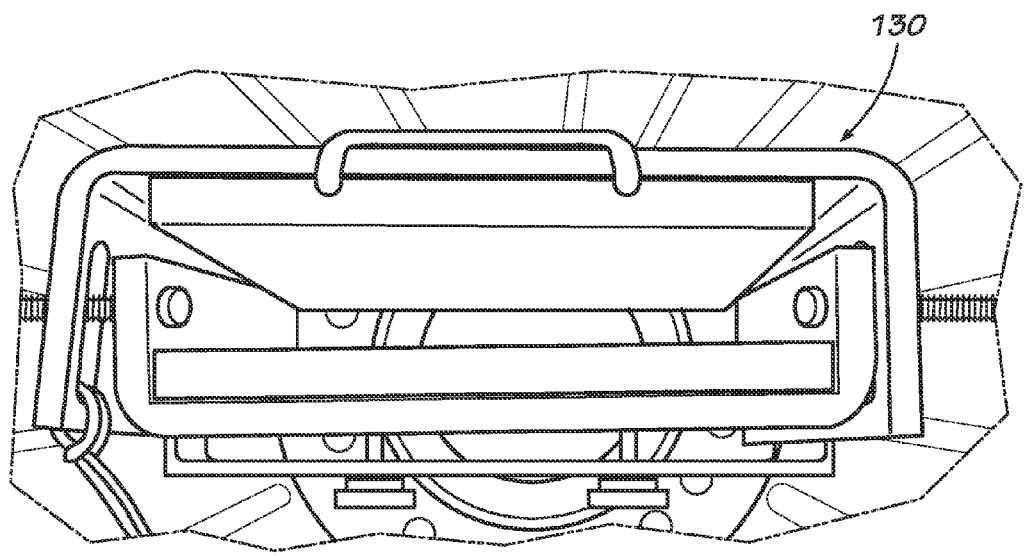

FIGS. 14A-14B show the adjustment feature of thumb-screws, which accommodate different palm thicknesses.

FIG. 14C shows the mounting of one of the two segments of the pivot rod 140. As noted elsewhere, the pivot rod 140 is in two segments. Note that only half of the globe 110 is shown for purposes of illustration.

Figure 15A:
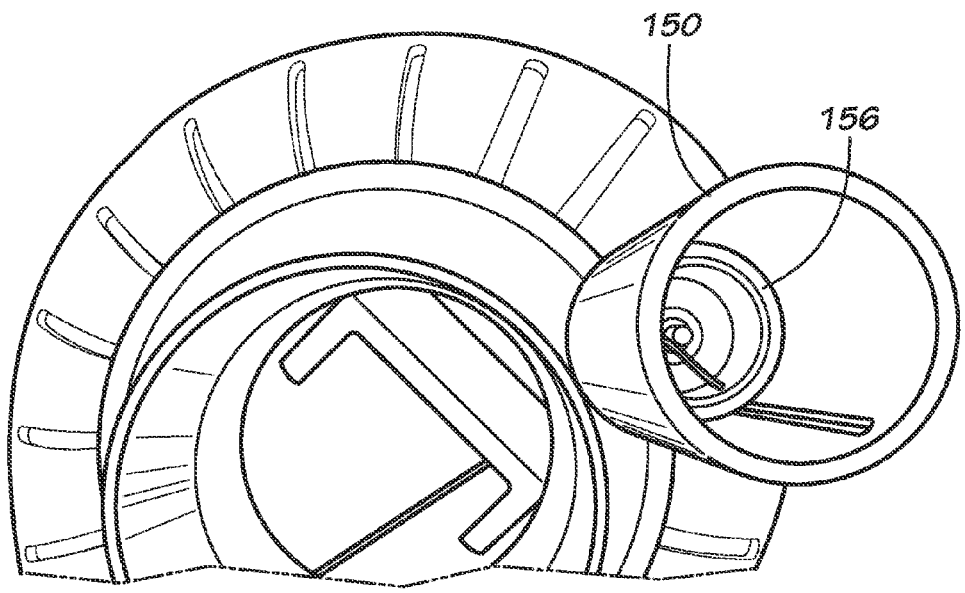
Figure 15B:
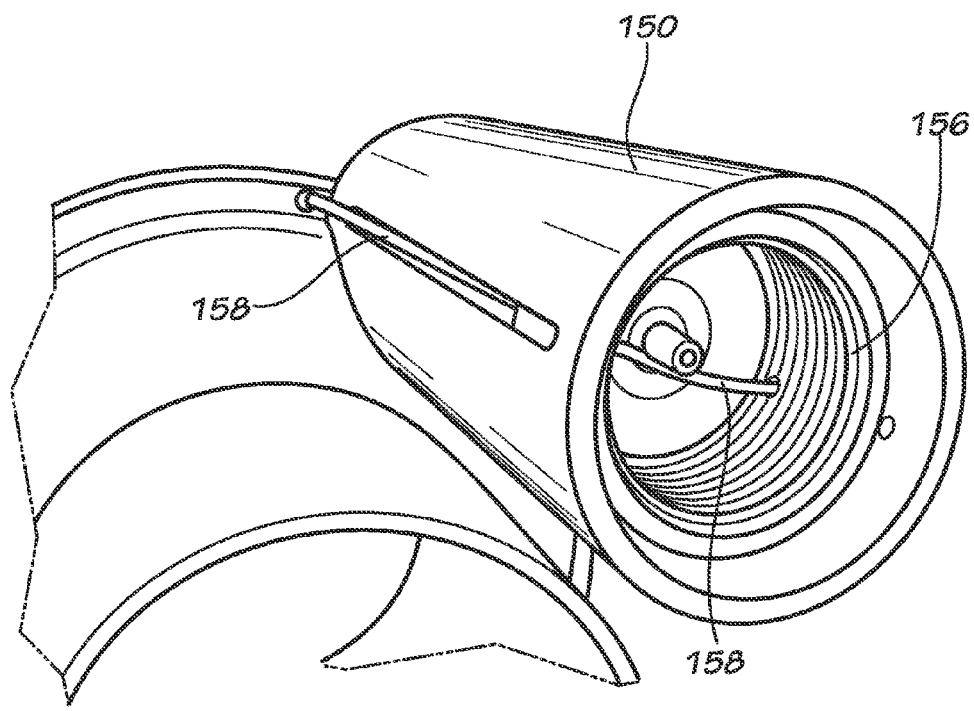

FIGS. 15A-15B show the movement of the sliding head member 156 from an "in" position (FIG. 15A) to an "out" position (FIG. 15A).

Figure 16A:
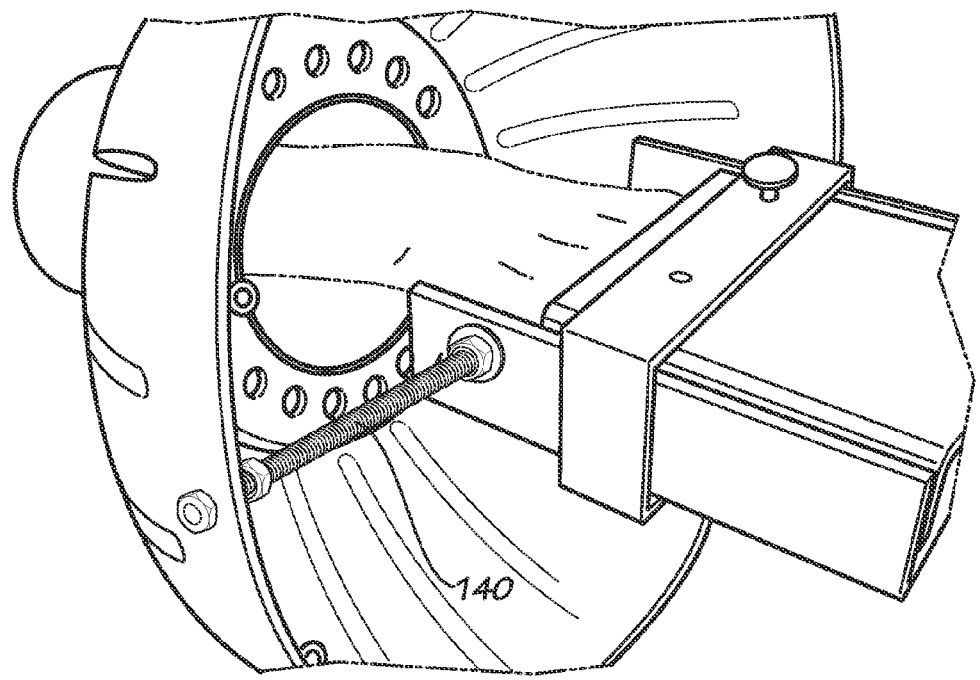
Figure 16B:
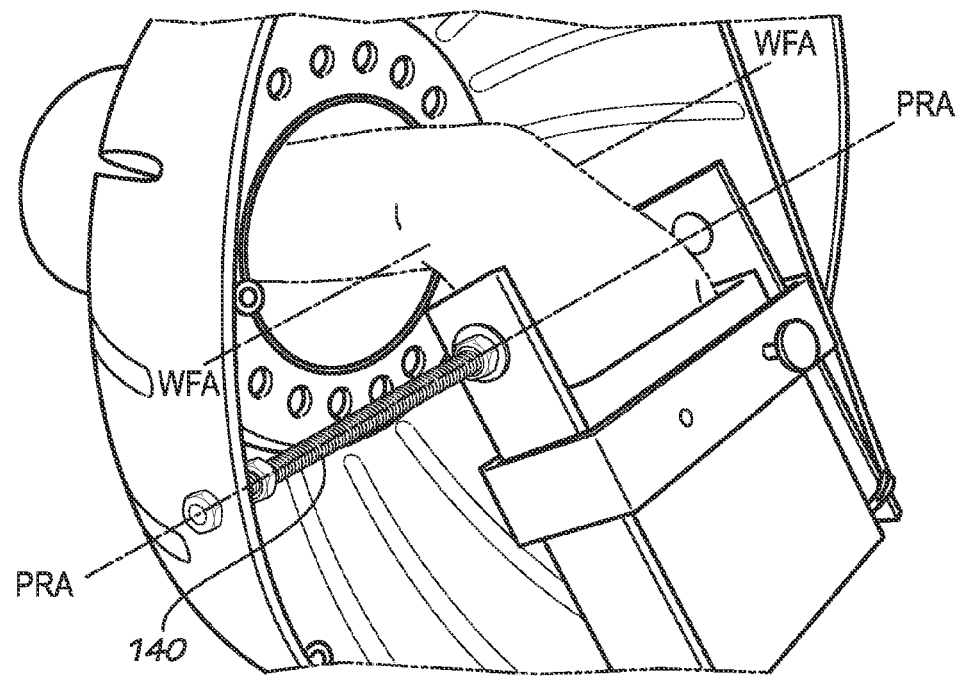

FIGS. 16A-16B show wrist flexion facilitated by the device 100. Note that wrist flexion axis (WFA) could more approximate pivot rod axis (PRA) if the hand is placed further in hand capturing member 130. Note that under one embodiment there is a preference that the WFA more closely match the PRA. However, due to the thickness of the hand, it has been found necessary to place the WFA proximal to the wrist in order to prevent the proximal aspect of the hand capturing member in the palm to impinge against the wrist.

Figure 17A:
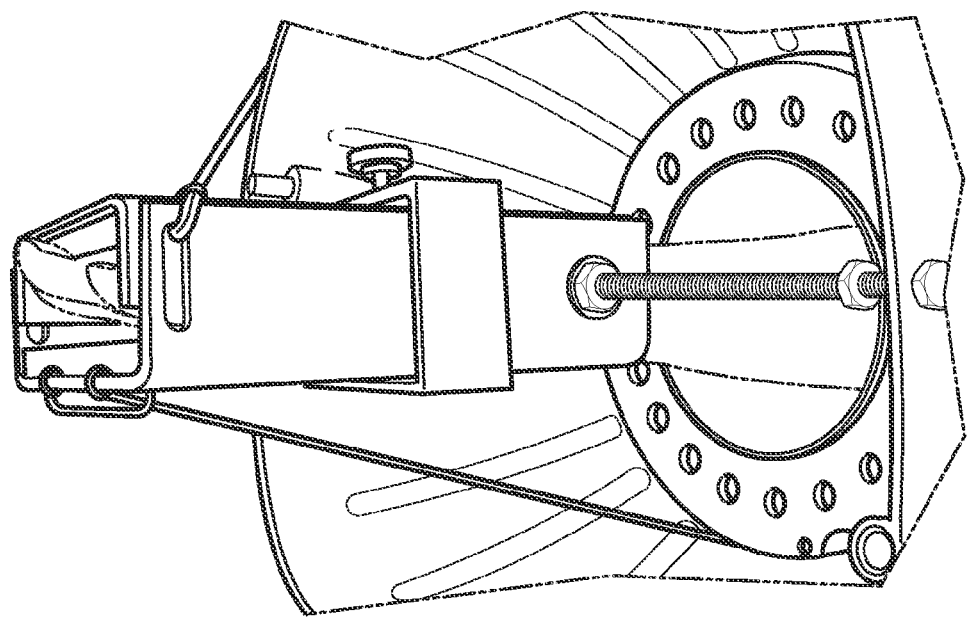
Figure 17B:
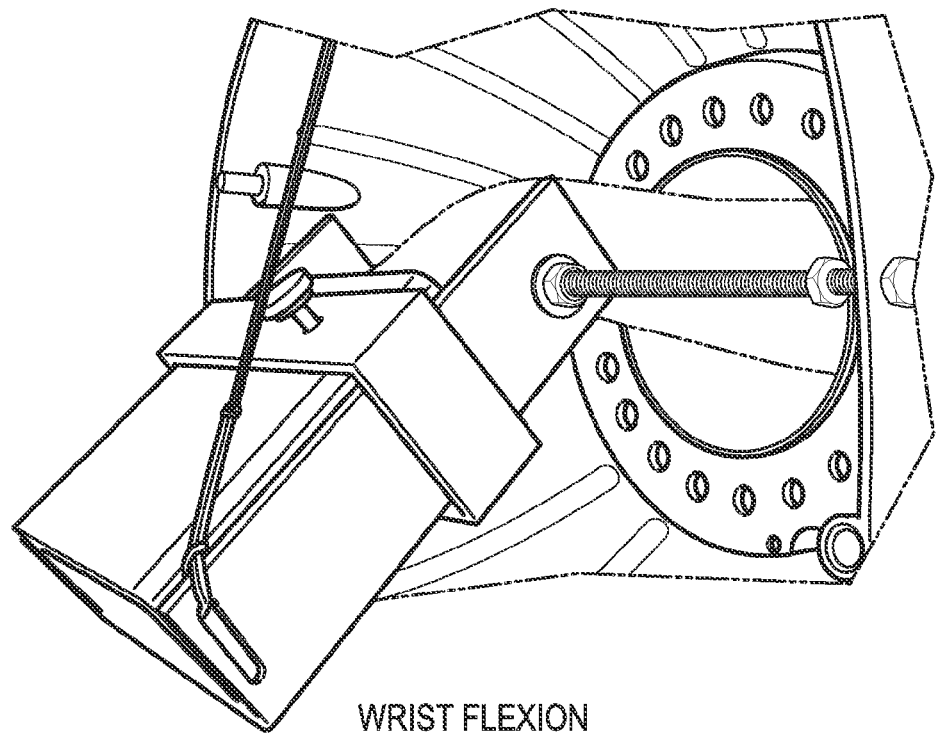

FIGS. 17A-17B show wrist flexion facilitated by the device 100, from a different point of view.

Figure 18:
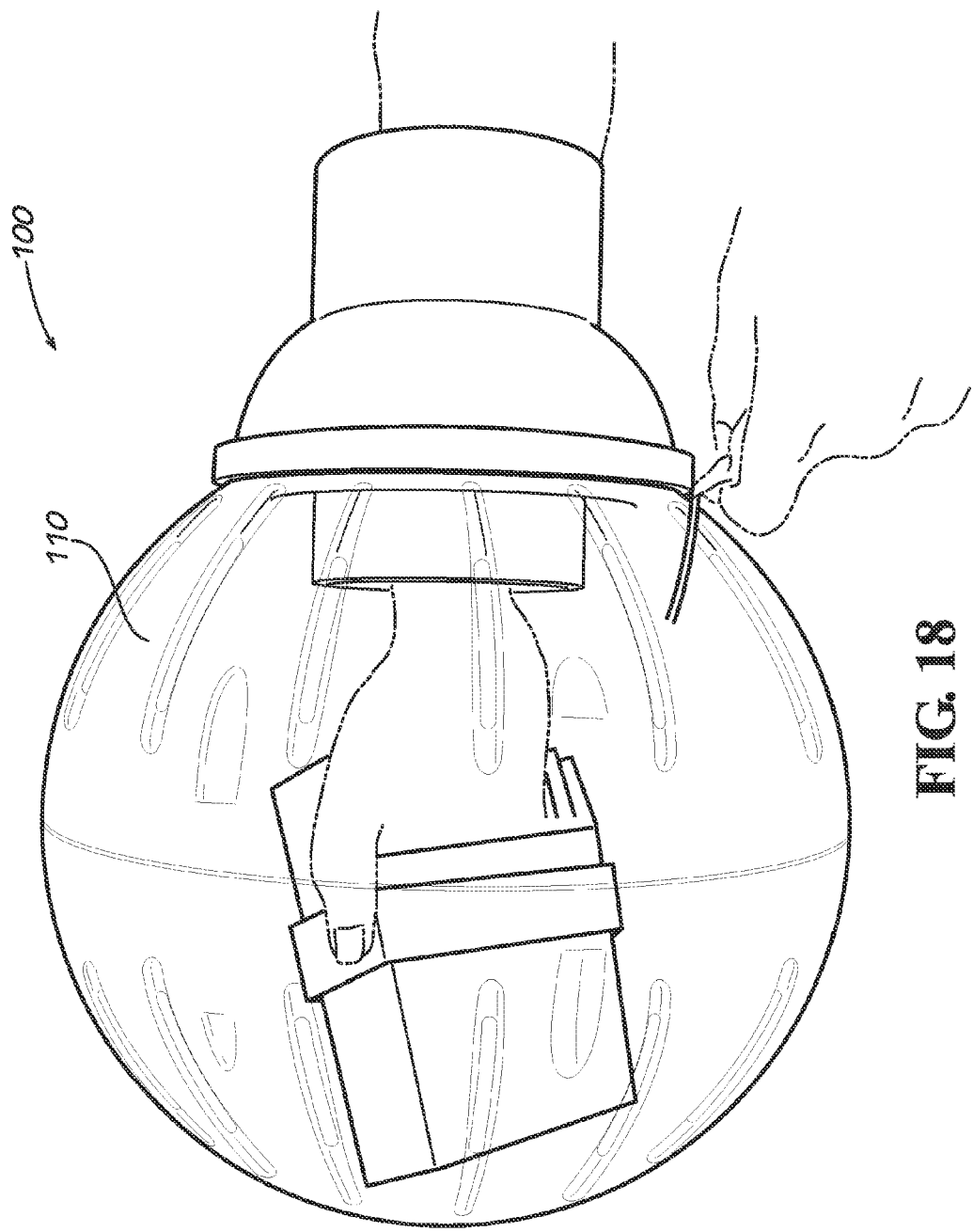

FIG. 18 shows the device 100 with the complete globe 110 shown, and the hand capturing member "extended" inside.

Figure 19:
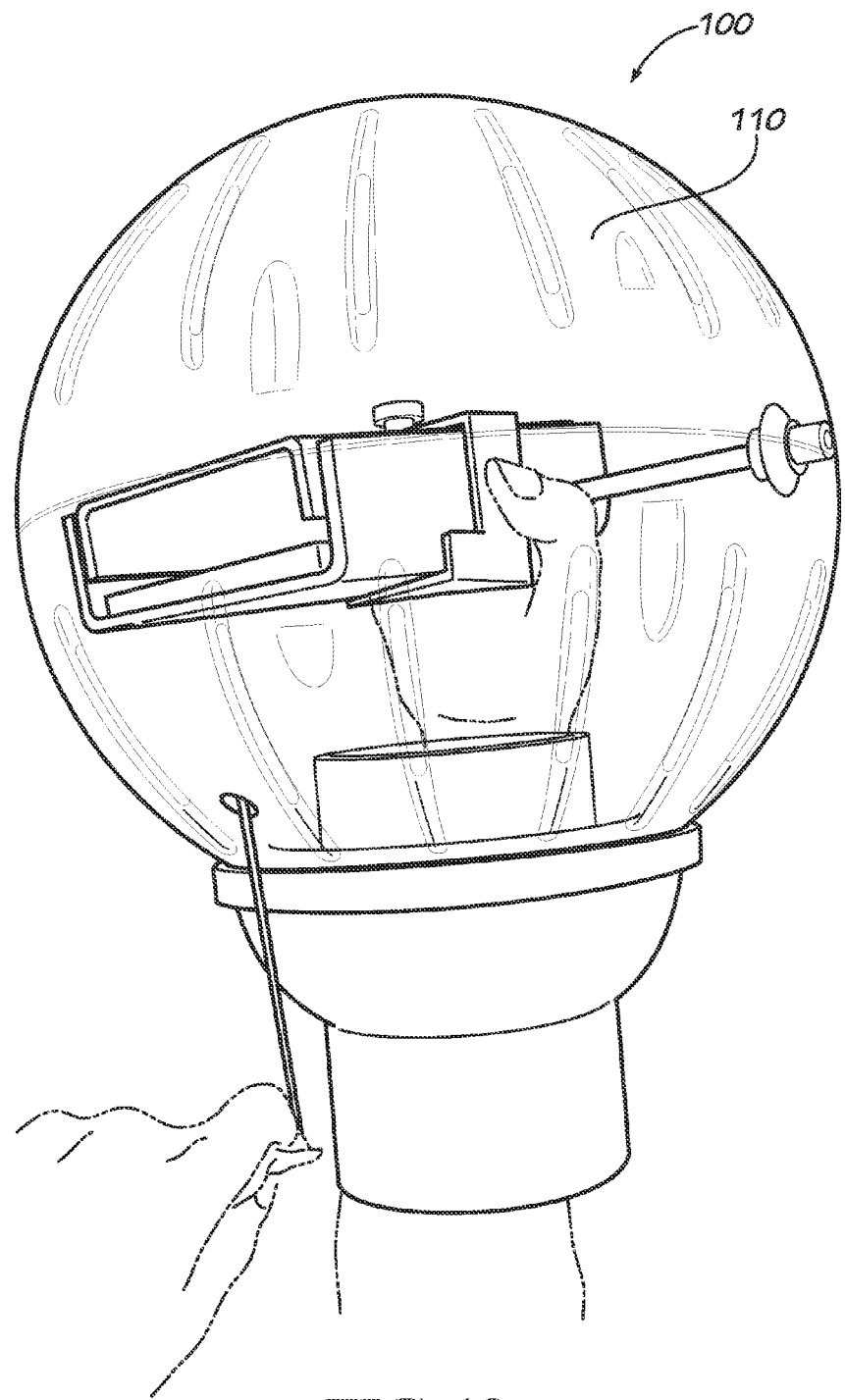

FIG. 19 is a view similar to FIG. 18, showing the hand capturing member more "flexed" inside.

Figure 20:
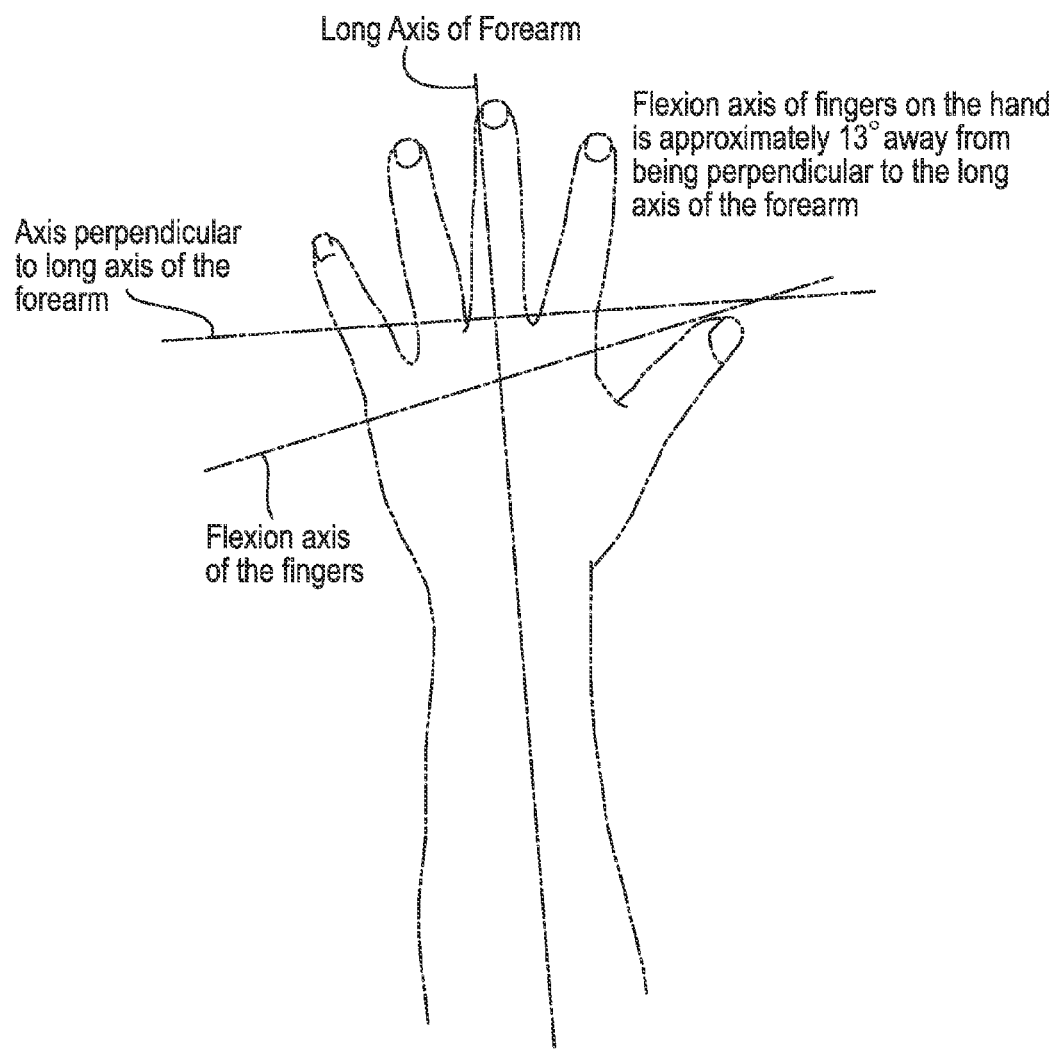

FIG. 20 shows the relationship between the flexion axis of the fingers, and the axis perpendicular to the longitudinal axis of the forearm. As may be seen, these two axes are at an approximately 13° relationship, as the axis of rotation of the 5$^{th}$ digit is closer to the wrist than that of the 2$^{nd}$ digit. The present invention accommodates this angular offset in accommodating flexion of the fingers.

Figure 21:
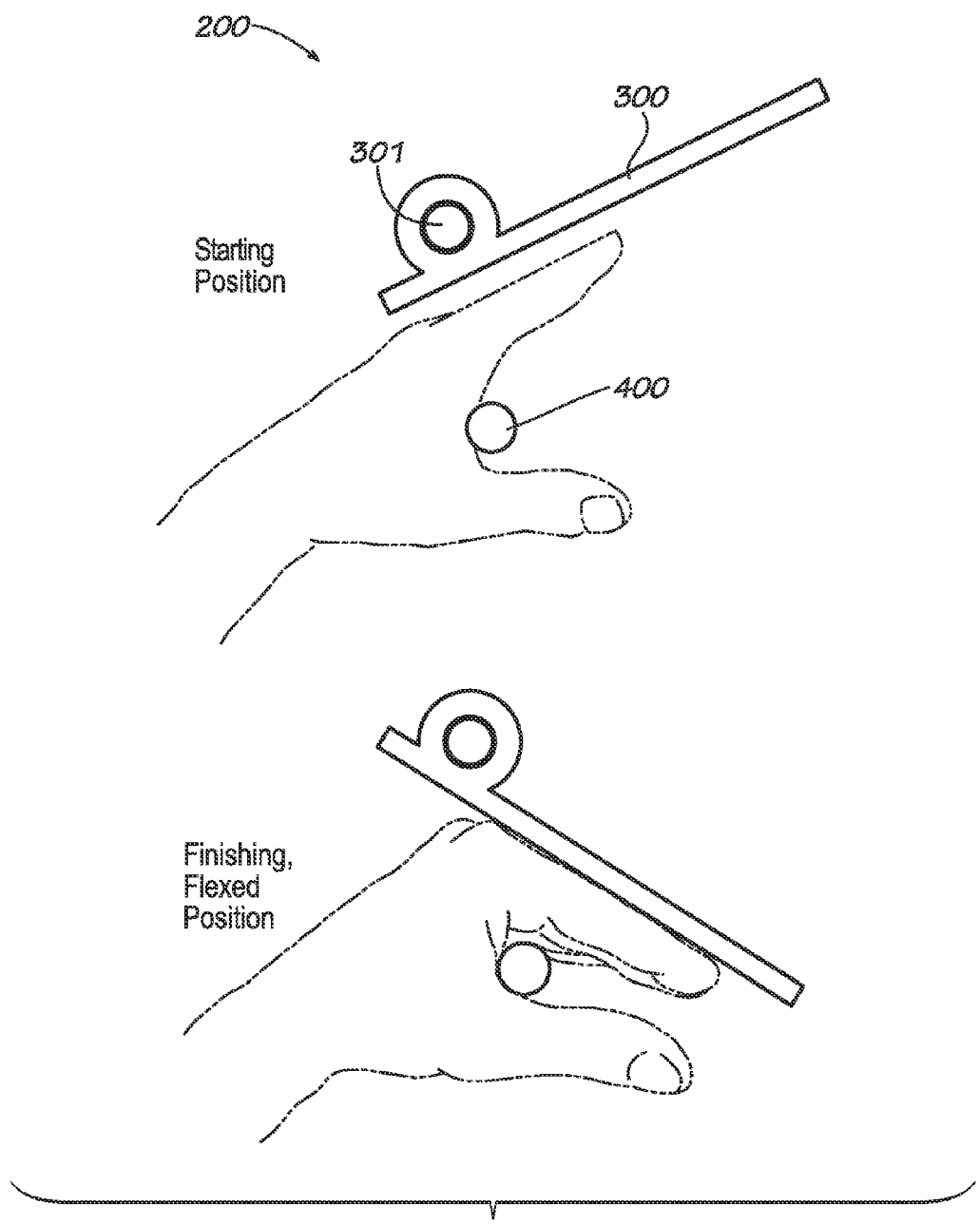
Figure 22:
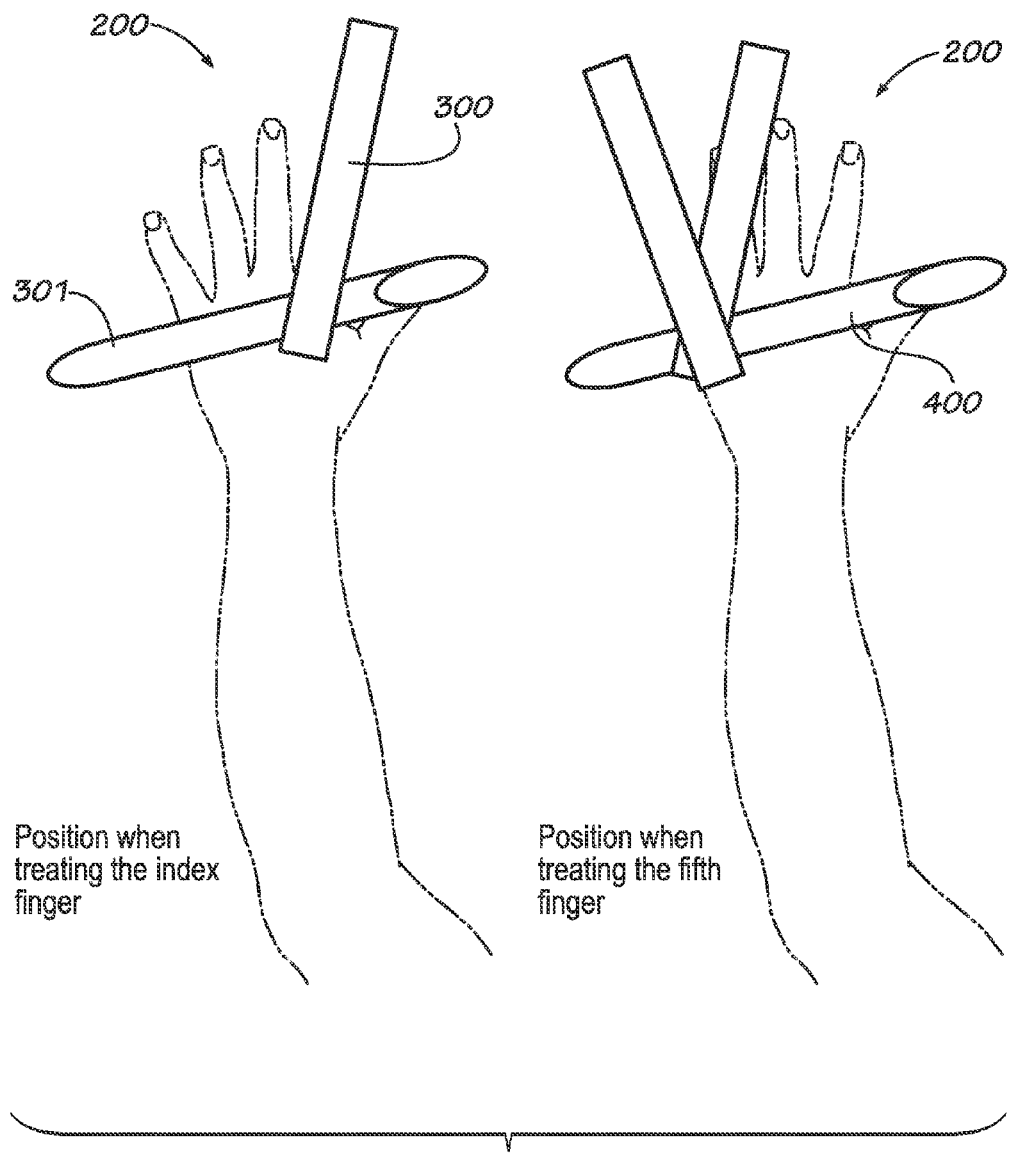

FIG. 21 shows via illustration the use of a distal capturing member 300 to flex an entire finger. A palm support member 400 (an elongate bar having its ends attached relative to the globe at a suitable location) is used to position and stabilize the hand. The distal capturing member 300 is rotatably (aka pivotably) mounted to an elongate rod 301 that has its ends attached to FIG. 22 illustrates how the fingers are aligned differently relative to each other, and are positioned on the hand at different locations. The present invention accommodates the different alignment by providing that the distal capturing member 300 has to be able to rotate in the coronal plane to account for different alignment of each finger. To account for different hand locations, the distal capturing member must also be able to translate along the longitudinal axis of the palm support member 400.

Figure 23:
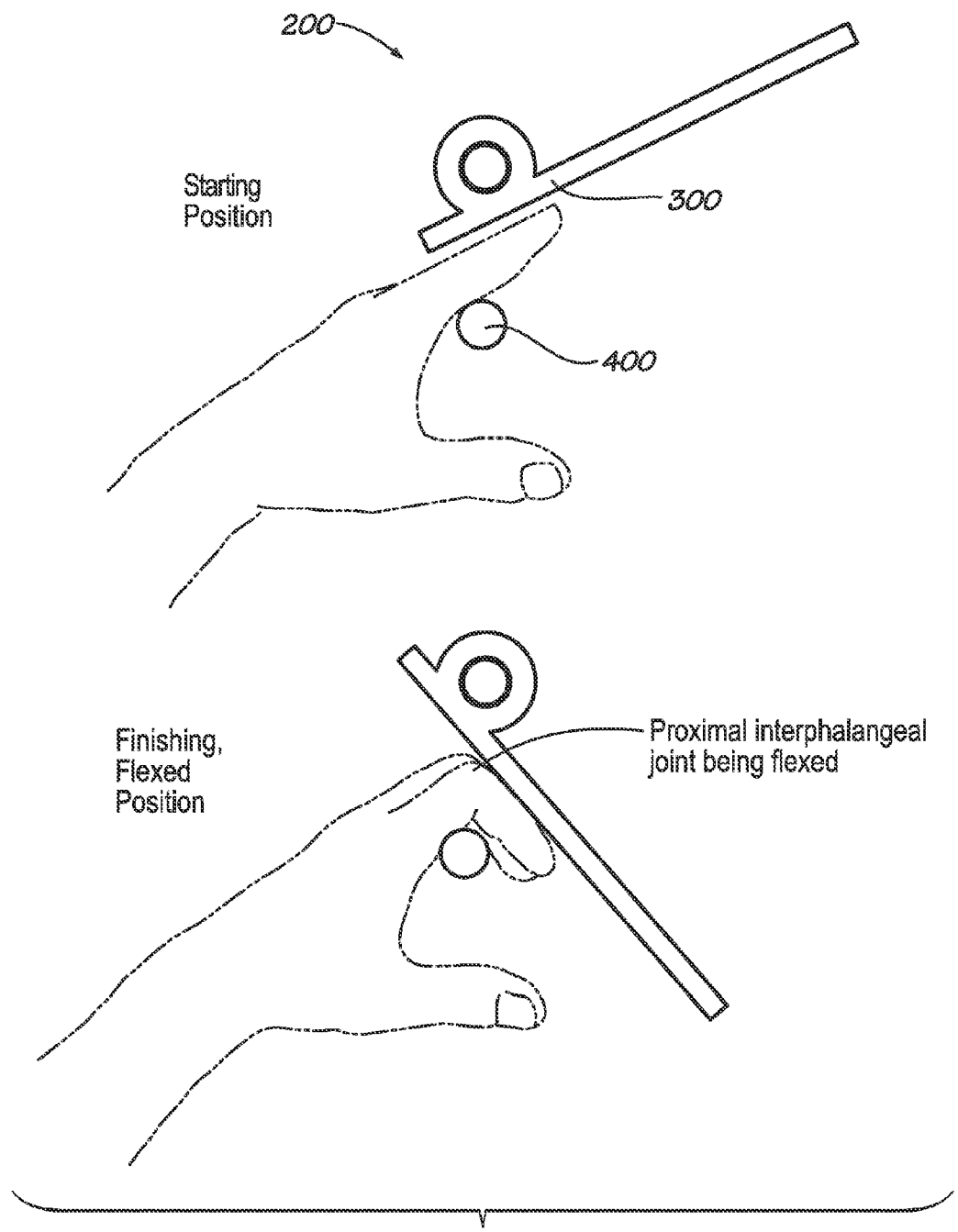

FIG. 23 shows the hand moved further back relative to the palm support member 400, such that the palm support member 400 is located under the proximal phalanx. Motion of the distal capturing member will then flex the proximal interphalangeal joint.

Figure 24A:
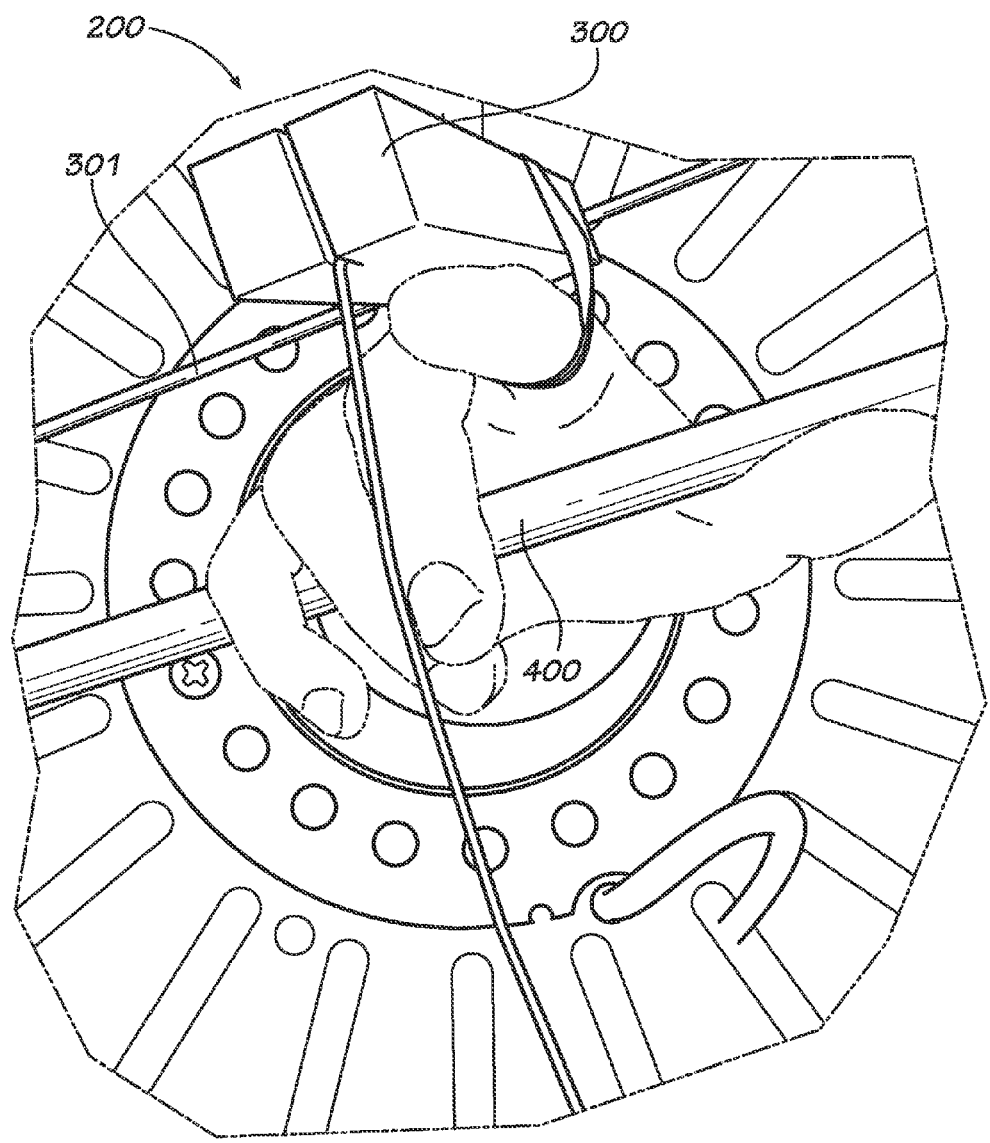
Figure 24B:
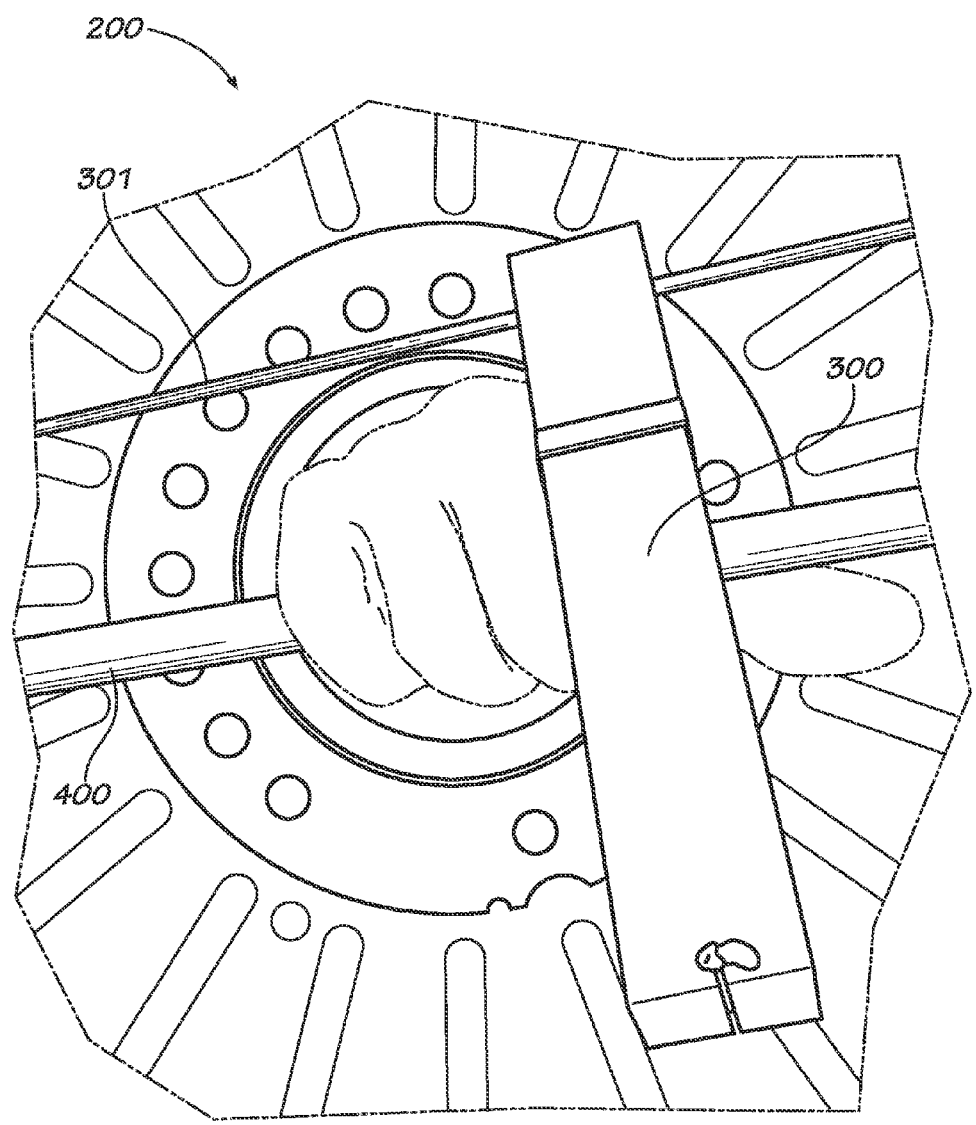
Figure 25:
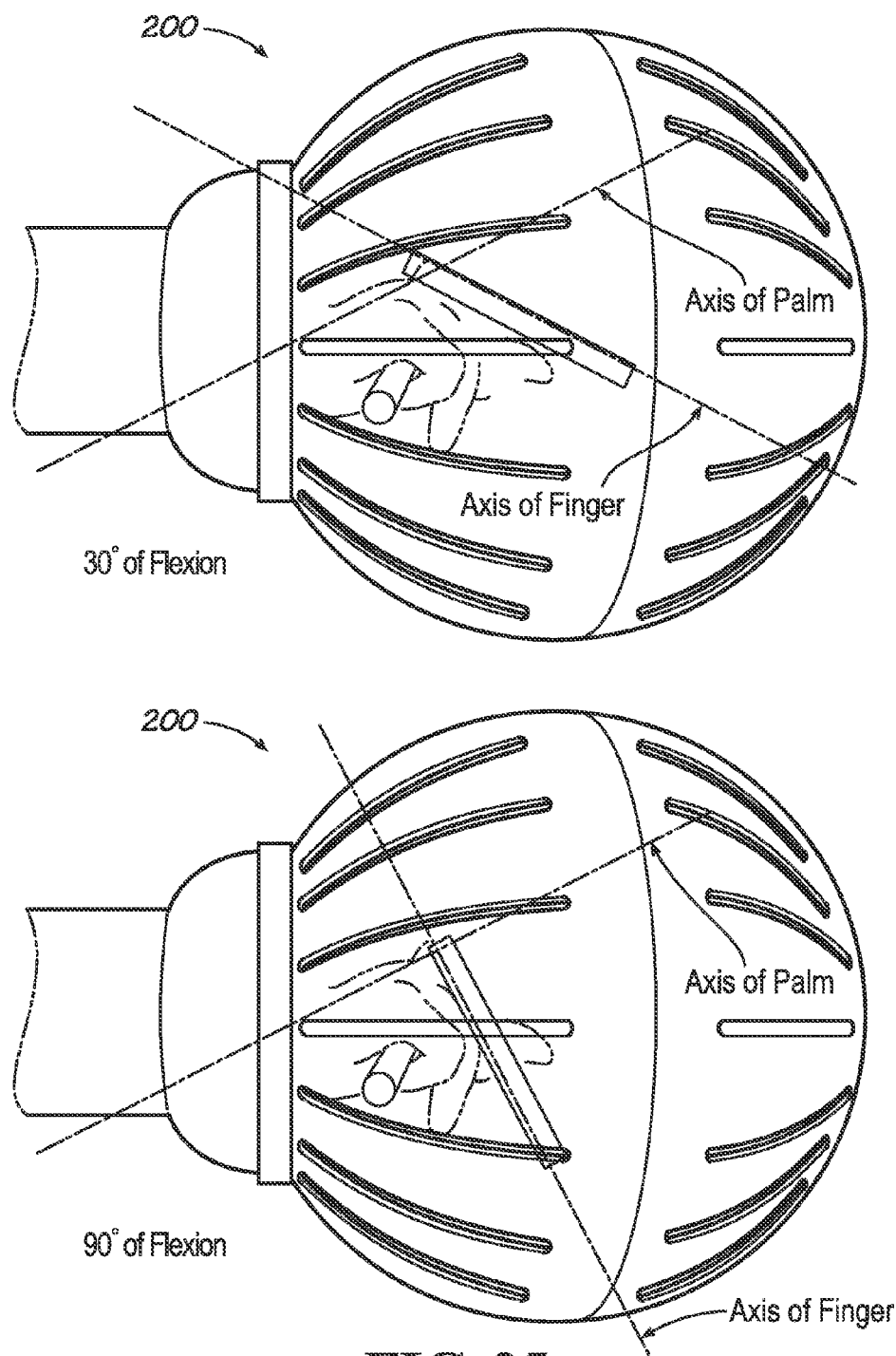

FIGS. 24A-24B show finger flexion of the forefinger, as an example. The distal capturing member FIG. 25 shows the finger globe system with a finger having approximately 30 and 90 degrees of flexion.

Figure 26:
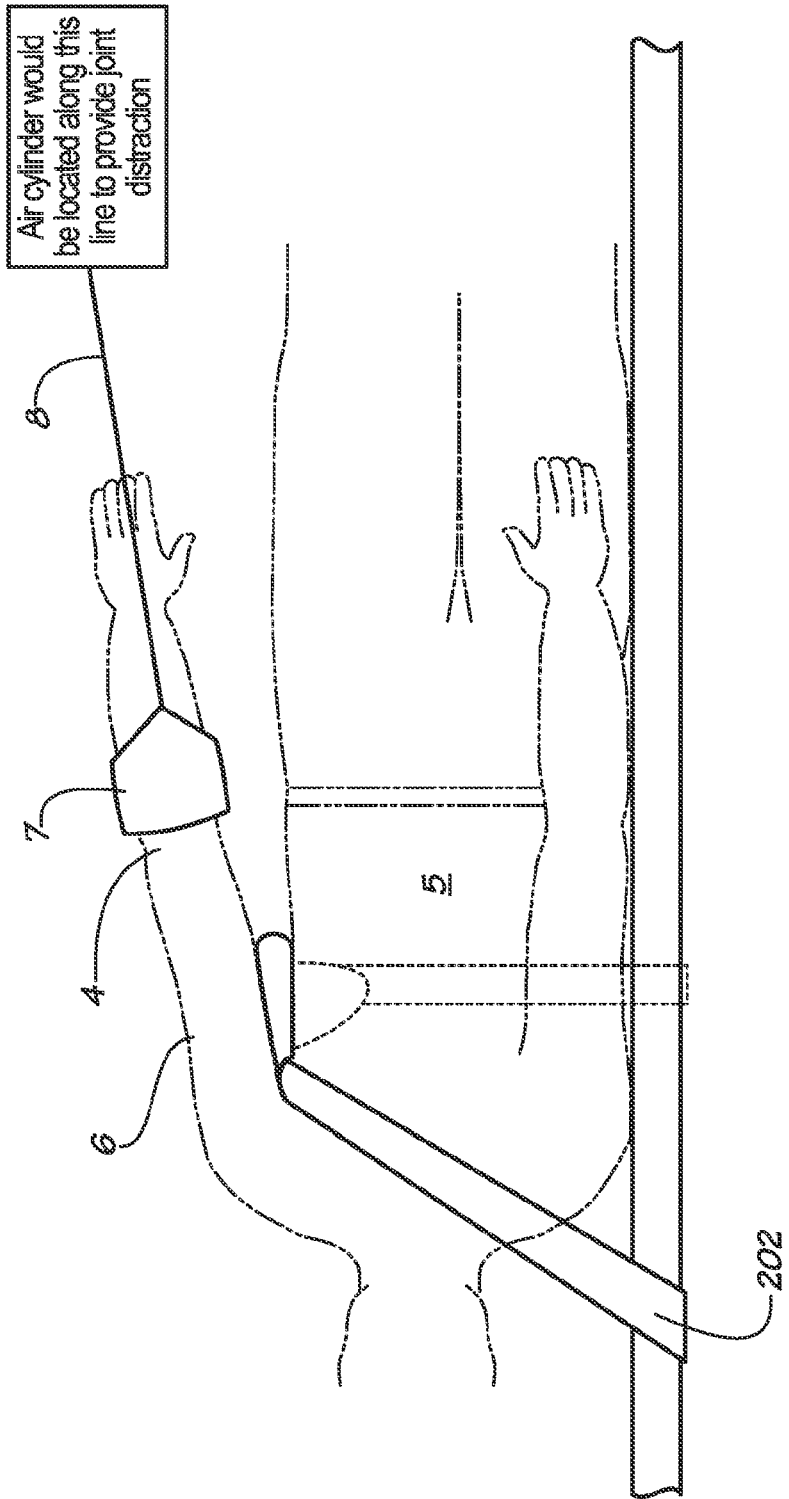

FIG. 26 shows the location at which the air cylinder (aka bladder driven linear actuator system 10) could be used to provide joint distraction.

FIG. 27 shows how two balloons may also be used within the cylinder in order to increase the travel of the sliding head member. A single balloon will have a limited amount that it can be inflated, thus limiting the amount of travel possible with the bladder driven linear cylinder. A second balloon can also be placed inside the cylinder in between the first balloon and the sliding head member, with a flexible air-tight hose passing through the sliding member to the balloon. The two balloons may then be simultaneously inflated to create linear motion of the sliding head member or sequentially inflated. Either simultaneous or sequential inflation of the two balloons will result in a two-fold increase in the linear travel of the sliding head member.

FIGS. 28A-29B show a cylinder assembly 500 similar to the bladder driven linear actuator system 10 described above, but configured to be attached relative to a patient's forearm and to provide flexion of an appendage such as a finger.

DETAILED DESCRIPTION OF VARIOUS EMBODIMENTS

I. General Overview

The invention generally is directed towards various embodiments of a bladder-driven linear actuator system for use with a variety of patient testing and measurement devices. Generally described, the various embodiments of the system include the use of an inflatable and deflatable balloon (e.g., a bladder), which is captured within a cylinder and a sliding head member. The balloon may be inflated with any number of manual or automated pumps or other inflation systems. Because air is trapped inside the balloon during inflation, the cylinder itself does not require an air-tight seal, and the sliding head does not need to seal tight to the inner diameter of the moveable external member (not shown in FIGS. 1A and 1B). If only one end of the tension string is attached to the moveable external member as shown, the other end of the tension string is fixed to or relative to the outer wall of the cylinder. In the configuration shown in FIG. 5 both ends are attached to the external member, which provides approximately double the force, but half of the stroke.

The present invention now will be described more fully hereinafter with reference to the accompanying drawings, in which some, but not all embodiments of the inventions are shown. Indeed, these inventions may be embodied in many different forms and should not be construed as limited to the embodiments set forth herein; rather, these embodiments are provided so that this disclosure will satisfy applicable legal requirements. Like numbers refer to like elements throughout.

II. Element List

10 Bladder Driven Linear Actuator System
   12 Cylinder Wall
   13 Fixed End Cap
   14 Inflatable/Deflatable Balloon
   16 Sliding head member
   18 Tension string
20 Bladder Driven Linear Actuator System 20 (FIGS. 2A and 2B)
   22 Cylinder Wall
   23 Fixed End Cap
   24 Inflatable/Deflatable Balloon
   26 Sliding head member
   28 Connecting rod
   29 External member
30 Bladder Driven Linear Actuator System 30 (FIGS. 3A and 3B)
   32 Cylinder Wall
   33 Fixed End Cap
   34 Inflatable/Deflatable Balloon
   36 Sliding head member
   38 Connecting rod
   39 External member
40 Bladder Driven Linear Actuator System 40 (FIG. 4)
49 external member
50 Bladder Driven Linear Actuator System 50 (FIG. 5)
59 external member
60 Bladder Driven Linear Actuator System 60 (FIGS. 6A and 6B)
69 External member
100 mechanical therapy device 110 globe
120 cylindrical forearm capturing member
130 hand capturing member
140 pivot rod
150 bladder driven linear actuator system
    152 Cylinder Wall
    153 Fixed End Cap
    154 Inflatable/Deflatable Balloon
    155 rubber bulb pump
    156 Sliding head member
    157 return rubber band (or spring etc)
    158 Tensioning string
    159 External member
300 Distal Capturing Member
301 Pivot Rod
400 Palm Support Member III. Outline A) The Bladder Driven Systems
1) Generally
2) Bladder Driven Linear Actuator System 10 (FIGS. 1A and 1B)
3) Bladder Driven Linear Actuator System 20 (FIGS. 2A and 2B)
4) Bladder Driven Linear Actuator System 30 (FIGS. 3A and 3B)
5) Bladder Driven Linear Actuator System 40 (FIG. 4)
6) Bladder Driven Linear Actuator System 50 (FIG. 5)
7) Bladder Driven Linear Actuator System 60 (FIGS. 6A and 6B)
8) Use to Move Other External Members B) Globe Systems
1) Generally
2) The Wrist Globe Systems
3) The Finger Globe Systems C) Joint Distraction Systems D) Miscellaneous IV. Details A) The Bladder Driven Systems 1) Generally Generally described, these systems according to various embodiments include the use of an inflatable and deflatable balloon (e.g., a bladder), which is captured within a cylinder and a sliding head member. The balloon may be inflated with any number of manual or automated pumps or other inflation systems. Because air is trapped inside the balloon during inflation, the cylinder itself does not require an air-tight seal, and the sliding head does not need to seal tight to the inner diameter of the cylinder. As the balloon is inflated, the sliding head member moves linearly within the cylinder.

2) Bladder Driven Linear Actuator System 10 (FIGS. 1A and 1B)

Reference is now made to FIGS. 1A-1B, which illustrate a bladder driven linear actuator system 10, which according to various embodiments comprises a linear cylinder driven by an interior inflatable balloon 14. The system 10 is comprised of 1) a cylindrical chamber defined by a cylinder wall 12;
2) a fixed end cap 13 on one end of the cylinder;
3) an inflatable/deflatable balloon 14 within the cylindrical chamber located inside the fixed end cap;
4) a sliding head member 16 located within the cylindrical chamber proximate the end of the balloon opposite to the fixed end cap;
5) a moveable external member (not shown in FIGS. 1A-B, but configured analogous to external member 29 of FIGS. 2A-2B, so as to move in response to movement of the sliding head member); and
6) an intermediate link connecting the cylinder with the external moveable member (in the version shown, a tension string 18 could be used, although compression elements could used such as solid connecting rod).

The balloon according to various embodiments may be inflated with any number of manual or automated pumps or other inflation systems. Because air is trapped inside the balloon during inflation, the cylinder itself does not require an air-tight seal, and the sliding head does not need to seal tight to the inner diameter of the cylinder. As the balloon is inflated the sliding head member moves linearly within the cylinder. During this inflation, a subcavity 19S of the cavity 19 at least partially defined by the cylinder wall 12 contains the balloon 14 (see FIG. 1A).

In at least the embodiment shown in FIGS. 1A-1B, the tension string 18 is inserted through horizontal slots in the barrel of the cylinder, and passes in front of the sliding head member. Shown is the use of a tension string, but in any of a variety of additionally envisioned embodiments, a belt, band, cable, or cord can be used to cause motion of the external member. Further, in certain embodiments, one or both of the ends of the tension string may be attached to the moveable external member (again, not shown in FIGS. 1A and 1B). In those embodiments in which only one end of the tension string is attached to the moveable external member as shown, the other end of the tension string may be fixed to or relative to the outer wall of the cylinder. For example, in at least the configuration shown in FIG. 5 both ends are attached to the external member, which provides approximately double the force, but half of the stroke. It should be understood, however, that alternative embodiments may be envisioned, as commonly known and understood in the art.

According to various embodiments, as best understood from FIGS. 1A-B, the linear distance that the sliding head member moves (e.g., its stroke distance) is approximately doubled by the tension string, thus doubling the distance traveled by the external member (stroke distance multiplied by 2). As an example, in at least the illustrated embodiment, 4" of sliding head movement would then result in 8" of motion of the external member. It should be understood that alternative stroke distances may be utilized, as desirable for any of a variety of particular applications.

In any of these and still other envisioned embodiments, the use of an inflatable/deflatable balloon 24 substantially eliminates the need for complex seals, as is customary with conventionally designed air cylinders. In addition, in certain embodiments, the elastic nature of the balloon allows for the external moveable member to slowly return to the initial start position in a controlled manner as the air is released from the balloon.

3) Bladder Driven Linear Actuator System 20 (FIGS. 2A and 2B)

This configuration includes the following elements:
    22 Cylinder Wall
    23 Fixed End Cap
    24 Inflatable/Deflatable Balloon
    26 Sliding head member
    28 Connecting rod
    29 External member According to various embodiments of the system 20, instead of the use of tension strings or the like, compression elements may be used such as a solid connecting rod 28. In at least certain embodiments, the rod 28 may be pushed/pulled by the sliding head member 26. This rod 28 may, in certain embodiments move straight along its longitudinal axis so as to push an external member (linearly as shown in FIGS. 2A and 2B), while in other embodiments it may be configured in a pivoting manner such as described later with respect to FIGS. 3A and 3B). Alternately, if timed and arranged right, the rod 28 according to still further envisioned embodiments could operate to move a rotating member much in the same manner as does a connecting rod in a common internal combustion engine (not shown).

According to various embodiments, as best understood from FIGS. 2A-B, the linear distance that the sliding head member moves (e.g., its stroke distance) is approximately equal to that traveled by the external member 29, as compared to the doubling effect provided by the tension strings of at least those embodiments illustrated by FIGS. 1A-B. For example, in the FIGS. 2A and 2B configuration, 4" of balloon inflation would result in 4" of motion of the external member.

According to various envisioned embodiments of the system 20 as illustrated in FIGS. 2A-B, the remaining various features, including but not limited to the cylinder wall 22, the fixed end cap 23, and the sliding head member 26 may be configured in size, shape, and orientation substantially similar to the cylinder wall 12, the fixed end cap 13, and the sliding head member 16, as previously described herein. In still other envisioned embodiments, each or any combination thereof these features may be substantially different than that previously described herein, as may be desirable for a particular application.

4) Bladder Driven Linear Actuator System 30 (FIGS. 3A and 3B)

This configuration includes the following elements:
32 Cylinder Wall
33 Fixed End Cap
34 Inflatable/Deflatable Balloon
36 Sliding head member
38 Connecting rod
39 External member As has been described previously, according to various embodiments as shown in FIGS. 3A-B, inflation of the balloon 34 may cause rotation of an external member 39, provided that the external member is fixed to an axis of rotation.

According to various envisioned embodiments of the system 30 as illustrated in FIGS. 2A-B, the remaining various features, including but not limited to the cylinder wall 32, the fixed end cap 33, and the sliding head member 36 may be configured in size, shape, and orientation substantially similar to the cylinder wall 12, the fixed end cap 13, and the sliding head member 16, as previously described herein. In still other envisioned embodiments, each or any combination thereof these features may be substantially different than that previously described herein, as may be desirable for a particular application.

5) Bladder Driven Linear Actuator System 40 (FIG. 4)

According to various embodiments, the configuration of system 40 includes elements substantially similar to those shown in FIGS. 1A-B and as discussed previously herein, but an additional element, an external member 49 is moved thereby, as illustrated in at least FIG. 4. In certain embodiments, one end of the string is attached to the external member 49. In those and other envisioned embodiments, if only one end of the tension string is attached to the moveable external member, the other end of the tension string may be fixed to or relative to the outer wall of the cylinder. This configuration creates a situation where the linear distance that the balloon is inflated (balloon stroke distance) is then doubled by the tension string, thus doubling the distance traveled by the external member (balloon stroke distance multiplied by 2). For example, according to various envisioned embodiments, four (4) inches of movement of the sliding head member (e.g., to the viewer's right) causes eight (8) inches of movement of the external member (e.g., similarly to the viewer's right).

6) Bladder Driven Linear Actuator System 50 (FIG. 5)

According to various embodiments, the configuration of system 50 as illustrated in at least FIG. 5 includes elements substantially similar to that shown in FIG. 4 and discussed previously herein. However, in certain embodiments of the system 50, both ends of the string are attached to the external member 59. In these and still other envisioned embodiments, such a configuration creates a situation where the linear distance that the balloon is inflated (e.g., the balloon stroke distance) is then matched by the tension string, thus equaling the distance traveled by the external member. In an exemplary embodiment, four (4) inches of movement of the sliding head member (to the viewer's right) causes four (4) inches of movement of the external member (to the viewer's right). However, it should be understood that in these and still other envisioned embodiments, the force against the external member approximates twice the string tension 59.

7) Bladder Driven Linear Actuator System 60 (FIGS. 6A and 6B)

According to various embodiments, the configuration of system 60 as illustrated in at least FIGS. 6A-6B includes elements substantially similar to that shown in FIG. 4 and discussed previously herein. However, in certain embodiments of the system 60, the external member is not moved linearly in the direction of string tension, but is instead mounted on a pivot, such that it can pivot or rotate upon being pulled upon by the string as shown in FIGS. 6A and 6B, provided that the external member is fixed to an axis of rotation. This configuration, as did that of FIG. 4, creates a situation where the linear distance that the balloon is inflated (balloon stroke distance) is approximately doubled by the tension string, thus doubling the distance traveled by the external member (balloon stroke distance multiplied by 2). For example, according to various envisioned embodiments, four (4) inches of movement of the sliding head member (e.g., to the viewer's right) causes eight (8) inches of movement of the external member (e.g., similarly to the viewer's right).

8) Use to Move Other External Members

According to various embodiments, the external member could be any of the moving members noted above, or other of a variety of member(s) needing movement, as may be desired for a particular application. It should be understood that such member(s), whatever their configuration and/or orientation, should be considered as contemplated within the scope of the present invention.

While not limited specifically to medical use, such systems as previously discussed herein and illustrated in at least FIGS. 1-6, may be incorporated according to various embodiments into disposable and/or durable medical devices intended to cause motion of a joint or limb to promote proper positioning during surgery or to promote proper rehabilitation following an injury or surgery. For example, these and still other envisioned systems could include any moving elements such as shown in the following patents: U.S. Pat. Nos. 6,669,660, 6,872,186, 7,479,121, and 7,547,289. Other suitable members in and out of the medical and/or therapeutic fields could also be used.

The aforementioned bladder driven cylinder (a.k.a. air cylinder) can be incorporated according to various embodiments into any of a variety of particularly inventive mechanical therapy devices, which may be intended to improve joint range of motion. As a non-limiting example, the cylinder may be employed for the purposes of stretching contracted tissue, wherein the proximal segment of a joint in one embodiment may be held in a constant position while the distal segment is moved. In these and still other envisioned embodiments, devices intended to increase joint range of motion may have an external member attached to the distal segment, such that moving the external member causes rotation about the desired joint thus stretching the targeted contracted tissue. In such instances, the aforementioned air cylinder according to any of the various embodiments described previously herein and further additionally envisioned, may be effectively used to provide the desired stretching torque, as inflating the balloon will cause the external member attached to the distal segment to rotate and stretch the tissue.

Figure 28A:
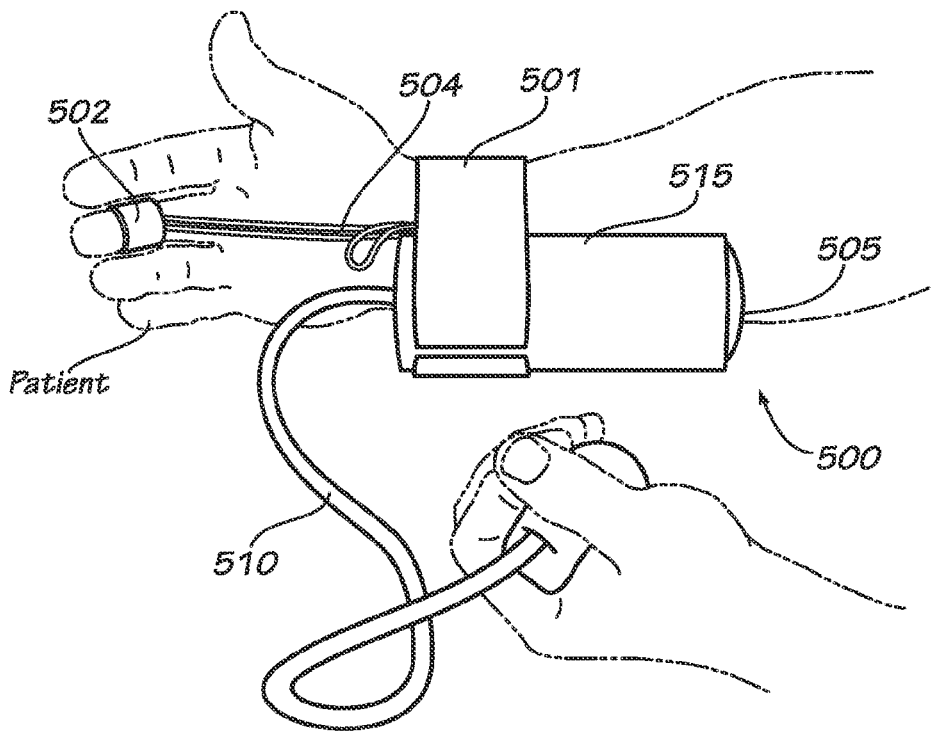
Figure 28B:
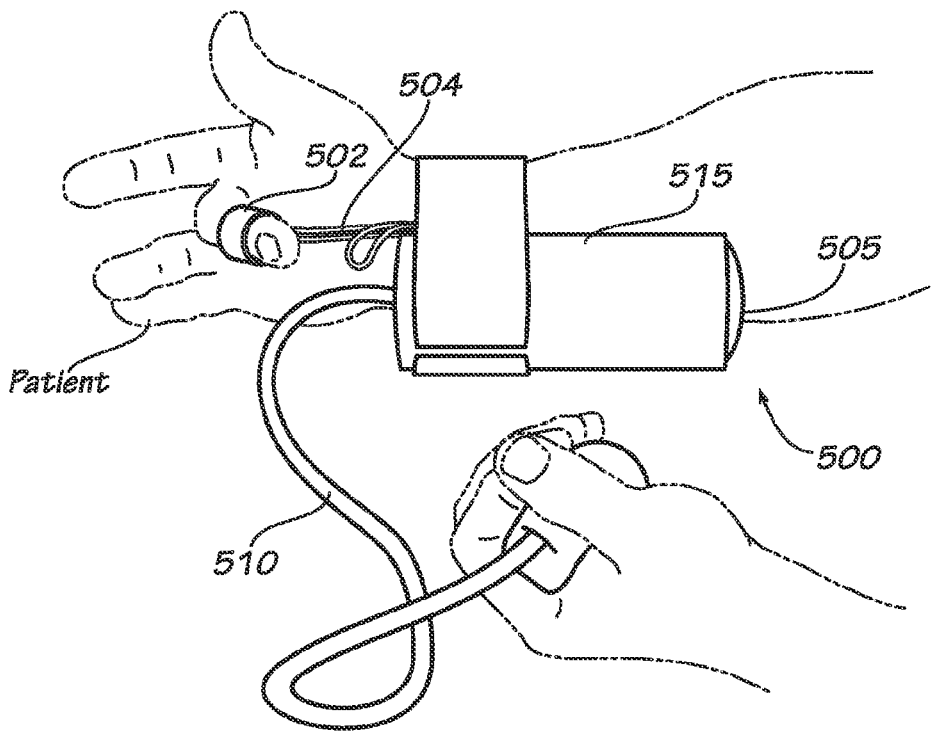

As yet another non-limiting example, the aforementioned bladder driven cylinder assembly (a.k.a. air cylinder) may be employed for the purposes of flexing contracted finger tissue, as generally shown in FIGS. 28A-29. In at least this and still other envisioned embodiments, the cylinder assembly (e.g., 500) may be configured such that it may be positioned substantially adjacent a patient's wrist, forearm, or other appendage. In certain embodiments, such as that illustrated, the cylinder assembly 500 may be physically attached and/or secured to the patient's wrist and/or arm. In at least the illustrated embodiment, the cylinder assembly 500 is attached to the patient's wrist or forearm via a strap 501, although it should be understood that in still other embodiments, the cylinder may be attached in any of a variety of ways, as commonly known and understood in the art, such as but not limited to other limbs or body parts for movement of nearby limbs or body parts.

Figure 29A:
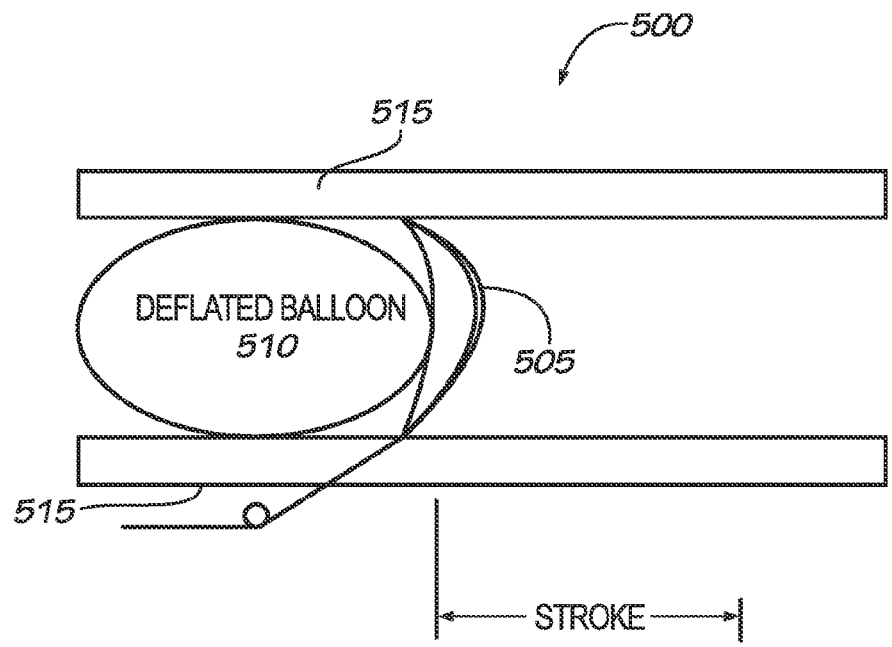
Figure 29B:
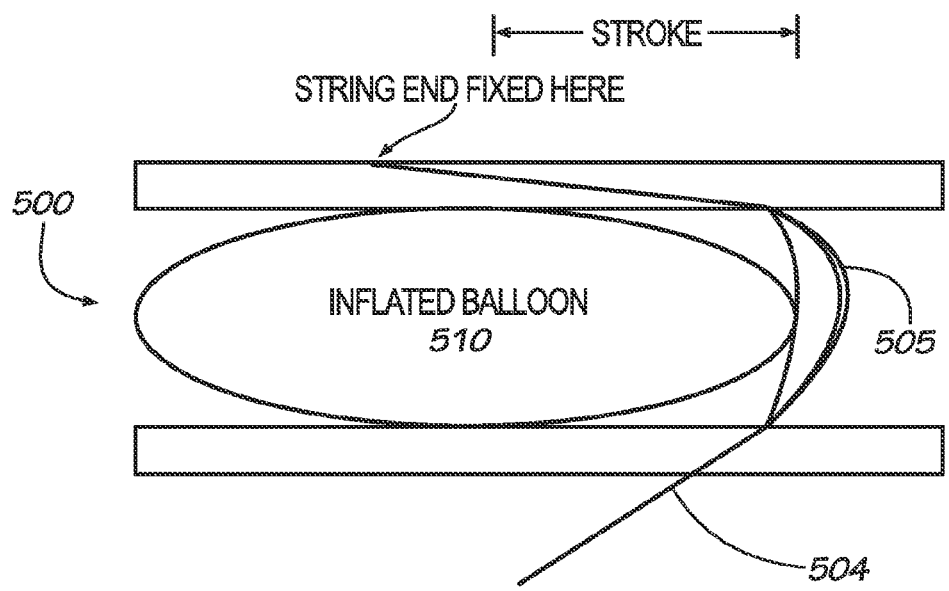

According to various embodiments, the cylinder assembly 500 may include a cap 505, a cylinder 515, and a bladder 510, as shown in at least FIGS. 29A-B. The cap 505 is according to various embodiments shaped and sized to be received substantially within and to slide along an interior circumference of the cylinder assembly 500. In certain embodiments, the cap 505 is positioned such that it travels, in use, away from the appendage (e.g., wrist, hand, or finger) being flexed. The bladder 510 is similarly shaped and sized so as to be received substantially within an interior of the cylinder assembly 500 (but for, of course, its pump 511), such that inflation of the bladder 510 according to these and still other envisioned embodiments causes the cap 505 to travel along a longitudinal axis of the assembly 500. In at least the illustrated embodiment, inflation of the bladder 510 causes the cap 505 to travel away from the appendage being flexed (see FIG. 28A extended finger versus FIG. 28B flexed finger positions), thereby enabling the travel of the cap to cause the desired degree of flexion.

According to various embodiments, the cylinder assembly 500 may be coupled to an external member 502 configured to capture one or more of the patient's appendages. While the illustrated embodiment includes a single external member 502 that encircles a single finger of the patient, alternative members may encircle, or otherwise grasp or retain, two or more fingers, thumbs, and/or wrists, or any combination thereof, as may be desired for a particular application. In this manner, in use, various embodiments cause flexion of the captured appendage by applying a desired level of force to the appendage in response to an inflation of the bladder 510 and a travel of the cap 505 along the cylinder assembly 500.

According to various embodiments, the cylinder assembly 500 may be coupled to the external member 502 via a string 504 (see FIGS. 29A-B). In certain embodiments, one end of the string 504 may be tied directly to the external member 502, while another, opposing end of the string may be configured to pass around at least a portion of the cap 505. In at least the illustrated embodiment, the cylinder assembly 500 may include at least one slot (not shown) that extends along at least a portion of the longitudinal axis of the assembly, thereby permitting the string 504 to pass from an exterior portion of the assembly into the interior for attachment to the cap 505, as described above. Although certain embodiments envision a cap 505 for attachment of the opposing end of the string, still other embodiments may instead dispense with the cap (or, alternatively, a piston or other comparable element) and merely attach the opposing end to an opposing internal or external side of the cylinder and/or to a portion of the bladder (not shown). In this manner, certain envisioned embodiments may involve at least a portion of the string 504 sliding over a portion of the surface of the bladder during use, or an end of the string could be attached to a portion of the bladder such that inflation of the bladder causes the portion of the bladder to move, which pulls on the string. In an alternative configuration, a rigid member can be attached to the bladder portion, and inflation pushes on the rigid member which itself pushes on or relative to a body portion.

Still further, in all of these and still other envisioned embodiments, the string 504 may be attached in any manner desirable provided inflation of the bladder 510 causes the string to move the external member 502 in such a manner as to cause flexion of the patient's appendage (e.g., finger(s), wrist, hand, etc.).

B) Globe Systems

1) Generally

As a non-limiting example, one type of a device using the aforementioned and described various embodiments of a bladder driven cylinder (a.k.a. air cylinder) system is a device which can be included in a "globe" system. In these and still other envisioned embodiments, such "globe" systems generally include the use of a hollow globe that substantially encircles the hand, with the globe having at least one through port which is configured to accept the distal end of the lower arm of a patient/user, as will be described in further detail below.

2) The Wrist Globe Systems

One non-limiting example of various "globe" systems that may, in accordance with various embodiments, be used together with any of the bladder driven linear cylinder systems of FIGS. 1-6 is a mechanical therapy device 100 as shown in at least FIGS. 7-19. Amongst other things, as will become evident herein, the device 100 is intended to assist with causing an increase in a patient/user's wrist range of motion.

According to various envisioned embodiments, the therapy device 100 generally includes the following subassemblies:
globe 110
cylindrical forearm capturing member 120
hand capturing member 130
pivot rod 140
bladder driven linear actuator system 150

As shown generally in FIGS. 7-19, the therapy device 100 according to various embodiments facilitates treatment of the wrist of a user (generally designated as 5 whenever shown) by the use of a hollow globe 110 (shown complete in some figures and in part in other figures for purposes of clarity). In certain embodiments, the hollow globe 110 may be configured to generally substantially encircle the hand of the user 5. In other embodiments, as may be desired for a particular application, the globe 110 may either fully encircle or merely partially encircle the patient/user's hand.

According to various embodiments, the globe 110 may further have at least one through-port provided by the cylindrical forearm capturing member 120. In certain embodiments, the member 120 may be configured to accept the distal end of the lower arm of a patient/user. In these and other envisioned embodiments, the forearm capturing member 120 may be rigidly attached relative to the globe (which could be considered the main frame of the device 100), while in still other embodiments, the member 120 may be selectively removably attached relative to the globe. In any of these various embodiments, it should be understood that the member 120 is generally configured to keep the forearm of the user 5 in a relatively constant position while the hand capturing member 130, positioned inside the globe, captures the hand of the user 5.

The hand capturing member 130 according to various embodiments is configured so as to be rotatably mounted relative to the globe 110, such that its axis of rotation PRA (see, for example, FIGS. 16A-B) is proximate the proximal portion of the hand capturing member 130. In this manner, according to certain embodiments, rotation of the hand capturing member 130 facilitates flexion of the wrist of the user, as may be further understood from FIGS. 17A-B, as a non-limiting example. In these and still other envisioned embodiments, the member 130 may be fixedly mounted relative to the globe 110 while in various additional embodiments, the two may be selectively removable from one another for purposes of, for example, maintenance and adjustment of the device.

According to various embodiments, the spherical or hemispherical shape of member 130 may further allow rigid rods (or the like) to be connected (either fixedly or selectively removably) relative to the proximal portion of the hand capturing member, as will be described in further detail hereinbelow.

Rotation of the hand capturing member 130 according to various embodiments may alternatively be facilitated by the bladder driven linear actuator system 150 (perhaps best understood from at least FIG. 10). In certain embodiments, the elements of the system 150 are substantially similar to those of the bladder driven linear actuator system 10, as described above. For example, in at least the illustrated embodiment, a tension string 158 of the system 150 pulls on the hand capturing member 130 such that it pivots about the axis of the pivot rod 140. In this manner, tension on the string causes flexion of the wrist. In these and still other envisioned embodiments, when the bladder is deflated, a return rubber band 157 (or other suitable spring or the like), as shown in at least FIG. 10, may be configured to encourage return to the extended wrist position.

Globe 110

According to various envisioned embodiments, the globe possesses a substantially globular shape, although in at least certain embodiments, it may be configured to be selectively broken apart to access the interior as needed. FIGS. 18 and 19, for example, show the complete globe 110, wherein FIGS. 7 and 12, for example, show a partial globe for illustrative purposes. In any of these and still other envisioned embodiments, the globe 110 may substantially encircle a portion or alternatively the entirety of a portion of a patient/user's limb, as previously described herein.

Cylindrical Forearm Capturing Member 120

Returning to FIG. 10, the cylindrical forearm capturing member 120 according to various embodiments is illustrated. In at least certain embodiments, the member 120 is configured such that it at least in part stabilizes the proximal segment of a user's forearm, as needed for a particular application, and thereby keeping the forearm at least stable and if needed fixed relative to the globe. It should be understood that the member 120, although illustrate as substantially cylindrical in shape, could possess any of a variety of alternative configurations, as desirable and/or necessary for a particular application, provided such is sufficient to keep the forearm appropriately stable and/or fixed relative to the globe, as previously described.

Hand Capturing Member 130

Remaining with FIG. 10, the hand capturing member 130 according to various embodiments is illustrated. In at least certain embodiments, the member 130 may be configured so as to grasp the palm section of the patient/user's hand such that movement of the hand capturing member 130 causes, at least in part, the desired flexion of the wrist. In these and still other envisioned embodiments, the sized of the opening of the hand capturing member 130 may be adjusted in thickness as needed, so as to accommodate various sizes of patient/user hands, as illustrated in, for example, FIGS. 11 and 12. In at least the illustrated embodiment, which may be more closely seen in at least FIGS. 13A-B and FIGS. 14A-B, such adjustment may be done via a "pin & slot" configuration, although any of a variety of adjustment mechanisms may be employed, as commonly known and understood in the art.

Pivot Rod 140

The pivot rod 140 according to various embodiments and as illustrated in, for example, FIG. 10 provides a pivot axis for the Hand Capturing Member 150. As may be seen, the pivot rod 140 of at least certain embodiments may comprise two segments. In these embodiments, each segment has one end attached to the globe and one end attached relative to the body of the hand capturing member 130, although in other envisioned embodiments, alternative configurations may be used, as desirable or necessary for a particular application.

Returning to at least the illustrated embodiment, which can be understood in further conjunction with FIG. 14-C, each of the segments may be fixed to one of the globe 110 or the body of the hand capturing member 130, and rotatably mounted to the other of the globe 110 or the body of the hand capturing member 130, such that the hand capturing member 130 can pivot (or rotate) relative to the globe 110 substantially about an axis that coincides with the coinciding longitudinal axes of the two segments. In at least one embodiment the free ends of the segments can be mounted at multiple locations depending on where the pivoting is desired relative to the globe 110.

Bladder Driven Linear Actuator System 150

According to various embodiments, the bladder driven linear actuator system 150 may contain elements configured substantially similar to those of the bladder driven linear actuator system 10 described above. In these and still other envisioned embodiments, the system 150 may comprise at least the following elements:

152 Cylinder Wall
153 Fixed End Cap
154 Inflatable/Deflatable Balloon
155 rubber bulb pump
156 Sliding head member
157 return rubber band (or spring etc)
158 Tensioning string
159 External member A tensioning string 158 according to various embodiments may be inserted through horizontal slots (not numbered, but illustrated in at least FIGS. 15A-B) formed in the cylinder wall 152. In this manner, the string 158 in at least certain embodiments passes substantially in front of the sliding head member 156. In at least the illustrated embodiment, the distal end of the tensioning string is fixedly attached to the distal end of the hand capturing member 130, while in alternatively envisioned embodiments the string may be selectively removably attached in any of a variety of ways, as may be desired for a particular application.

In any of these and other envisioned embodiments, a rubber bulb pump 155 may further be attached relative to the balloon, such that squeezing of the balloon 155 causes the balloon to inflate, which results in the linear movement of the sliding head member 156 relative to the cylinder wall 152 (see FIGS. 8-10 for example). In at least certain embodiments, the linear travel of the sliding head member 156 likewise results in rotational movement of the hand capturing member, thus increasing the angle of the wrist.

As a non-limiting example, in the treatment of joint contractures, the patient generally needs to be treated daily in order to create lasting gains in range of motion. In one such treatment protocol, the patient, when using an exemplary "globe" system may be asked to inflate the balloon 155 using the hand bulb until the hand capturing member rotates to a position in which the patient feels a comfortable stretch. In certain embodiments, the patient may then be asked to maintain this position for 5 to 15 minute intervals. If during the course of a treatment interval, the intensity of the stretch diminishes as the tissue is lengthened, patients may then be instructed to again squeeze the hand bulb to maintain the most effective stretching intensity. Patients are then asked to repeat the 5 to 15 minute stretching interval throughout the day in order to achieve 60 minutes of end range stretching per day. Of course, alternative methods of treatment and protocols for the same may be employed, as contemplated within the scope of using the devices of the present invention.

3) The Finger Globe Systems 200

Yet another non-limiting example of various "globe" systems that may, in accordance with various embodiments be used together with any of the bladder driven linear cylinder systems of FIGS. 1-6 is a finger globe system 200 as shown in at least FIGS. 21-25. Amongst other things, as will become evident herein, the device 200 is intended to assist with causing an increase in a patient/user's finger range of motion.

According to various envisioned embodiments, the system 200 may generally include the following subassemblies:
  Distal Capturing Member 300
  Pivot rod 301
  Palm Support Member 400

In other envisioned embodiments, the system 10, as previously described herein, may be used to increase finger motion. However, in any of these and still other envisioned embodiments, it should be understood that the various Finger Globe Systems (e.g., 200) generally feature an air cylinder, a method to stabilize the proximal segment, and a method to capture the distal segment in such a way that allows the air cylinder to pull a tensioning string causing rotation of the contracted joint, as have been generally described previously herein with regard to various other systems.

According to various embodiments, the finger device may also use a spherical or hemispherical exterior member to allow for multiple angles for the axis of rotation. This can be set and adjusted as such that the axis of rotation is set 13° from being perpendicular to the longitudinal axis of the forearm. As illustrated in FIG. 20, this approximates the hand's natural flexion axis, as the axis of rotation of the $5^{th}$ digit is closer to the wrist than that of the $2^{nd}$ digit.

Unlike the wrist device described above, the finger device according to various embodiments generally does not attempt to move the entire hand, but instead primarily attempts to individually move a single joint on a single finger. In certain embodiments, this is accomplished by the use of a distal capturing member 300, such as that shown in at least FIG. 21, which captures the finger while still allowing for the desired movement. Movement of the distal capturing member about an associated pivot rod 301 (see also FIG. 21, and having its ends attached to the globe) causes movement of the associated finger. As will also be understood in further detail below, any of a variety of other supports may be used to properly position the remainder of the hand in these and still other envisioned embodiments.

In order to achieve its movement of a single joint according to various embodiments, the distal capturing member must generally be configured so as it is capable of movement in at least three (3) degrees of freedom. In certain embodiments, the primary axis of rotation must generally remain free to move throughout use, whereas the other two degrees of freedom are used at the beginning of a treatment period to properly align the distal capturing device on the desired joint to be treated. In these and still other envisioned embodiments, these latter two degrees of freedom may likewise remain free during adjustment, but may also in at least certain embodiments be secured in location to ensure consistent proper alignment throughout the treatment period.

The primary axis of rotation is the axis that the member 300 must rotate about in order to flex and extend the finger or finger portion, as illustrated in at least FIG. 21. In at least the illustrated embodiment of that figure, the primary axis is the longitudinal axis of the rod 301. As may be understood this axis may be adjusted by attachment to different locations inside the globe, as may be desired for any of a variety of particular applications, as further shown in at least FIGS. 24A-B.

According to various embodiments, the distal capturing member 300 must be able to translate medially and laterally along the primary axis of rotation in order to isolate the individual finger. In at least the illustrated embodiment of FIG. 22, the member 300 must also be able to rotate in the coronal plane in order to account for each finger's alignment in relation to the long axis of the forearm. These two movements are, in these and still other envisioned embodiments, movements only done during adjustment of the device to fit the hand.

It should further be understood that by allowing the distal capturing member to have 3 degrees of freedom according to various embodiments, the $2^{nd}$ through $5^{th}$ digits of a patient/user's hand may all be treated appropriately according to the patient's natural alignment.

FIG. 23 further shows the hand moved further back relative to the palm support member 400 according to various embodiments, such that the palm support member 400 may be located under the proximal phalanx. In these and other envisioned embodiments, motion of the distal capturing member 300 will then flex the proximal inter-phalangeal joint in conjunction with the palm support member 400. Similarly, in still further envisioned embodiments, repositioning the hand even further back so the palm support member is underneath the intermediate phalanx may allow the motion of the distal capturing member to flex the distal interphalangeal joint (not shown).

It should be understood that an inability to correctly align the axis of rotation of a portion of the person's body with the person's natural rotational axis will result in rotation about an unnatural axis of rotation, either limiting the ability of the device to treat the patient's condition or potentially placing unintended rotational stress on tissues not involved with the joint contracture. As such, the member 300 according to various embodiments of the invention, however, configured, shaped, or sized, must be such that, at a minimum, proper alignment about an axis of rotation of a portion of the patient/user's body is attainable, as illustrated in at least FIG. 25.

In at least certain embodiments, the use of the spherical or hemispherical exterior member allows the health care provider to realign the axis of rotation as holes or slots can be placed in any position in the globe in order to accommodate the wrist-pivot or finger-pivot related member described herein. This allows an infinite number of potential axes that can be used, thus allowing for the axis of rotation to be perfectly aligned for each individual patient.

4) Various Methods of Using the Above-Described Globe Systems Generally

For all of the joints mentioned above, a treatment protocol similar to the previously described 60 minutes/day would effectively increase joint range of motion.

In all embodiments of both the wrist and finger devices, many methods may be utilized to capture and/or stabilize both the segment proximal to and distal to the contracted joint. Both the proximal and distal members can be adjustable to account for variability in finger, hand, and forearm dimensions between patients. In the wrist system, the hand capturing member can made in different sizes for different sized hands, or can made to be adjustable with set screws or elastic components such as the thumb-operated thumbscrews depicted in FIGS. 14A and 14B. As the screws are tightened, the volar aspect of the hand capturing member is brought closer to the palmar component, thus allowing the device to accommodate smaller hand sizes. In the finger system, this can be accomplished by using an elastic sleeve that the finger is inserted into as the patient positions themselves in the device. The sleeve would be attached beneath the rigid moveable member to ensure proper positioning of the finger within the system. One or multiple Velcro straps may also be used to secure the finger to the moveable member, and would again allow for varying finger sizes.

For both the finger and wrist devices, both the proximal and distal capturing/support members may also be customized by a health care professional to match each patient. In one embodiment, these customized capturing/support members can be formed with currently marketed heat-moldable plastics, either with or without the use of foam inserts to provide cushioning to prevent areas of high pressure to prevent excess stress and the risk of skin breakdown.

C) Joint Distraction Systems

The Bladder Driven Linear Actuator System 10 according to various embodiments may also be used to provide joint distraction, as shown in at least FIG. 26. As was described above and depicted in see FIGS. 1A-B, the air cylinder may be used to create linear travel of an external member. This may be very useful in creating joint distraction. During surgery, such as arthroscopic shoulder surgery, the joint may need to be distracted to create additional space within the joint. This additional space creates additional room for surgical tools to be inserted in the joint space while reducing the risk of damaging surrounding soft tissues or articular cartilage.

The conventional method to distract the joint is to attach an external member to the hand and wrist, which is then attached to a string and pulley system. A static weight is then attached to the opposite end of the string to provide a constant distraction load. However, this technique does not take into account differ patient body sizes. A 10 pound weight will cause much greater distraction the shoulder of a pediatric patient or frail, elderly patient than it would a 6'2", 280 pound industrial worker.

In contrast to these conventional methods, the use of the Bladder Driven Linear Actuator System 10 would allow for varying levels of force to be applied for each individual patient. By placing a graded scale on the exterior of the wall of the air cylinder, health care professionals could monitor the distance that the joint is distracted, thus creating consistent, reproducible operating conditions for all patients no matter his or her height and weight.

In certain embodiments, a Velcro strap would be placed around the patient's proximal upper arm, just distal to the elbow. One side of the tensioning string could be attached to the lateral aspect of the arm strap and the other attached to the medial aspect of the strap. Then, as the balloon was inflated with the hand bulb, shoulder joint distraction would occur (such as shown in FIG. 26). In still other envisioned embodiments, the Velcro strap could be placed immediately proximal to the elbow. Similar methods and devices could be utilized for other joint such as the ankle, knee, hip, wrist, or fingers.

In addition, similar methods and devices could be utilized according to various embodiments previously described herein and further envisioned to provide the distraction necessary to reduce a displaced fracture or when resetting a fracture. Similar methods and devices could then be used to treat tibial, femoral, radial, ulnar, and humeral fractures.

D) Miscellaneous

As shown in at least FIG. 27, two balloons may also be used according to various embodiments within the cylinder in order to increase the travel of the sliding head member. A single balloon will have a limited amount that it can be inflated, thus limiting the amount of travel possible with the bladder driven linear cylinder. A second balloon can also be placed inside the cylinder in between the first balloon and the sliding head member, with a flexible air-tight hose passing through the sliding member to the balloon. The two balloons may then be simultaneously inflated to create linear motion of the sliding head member or sequentially inflated. Either simultaneous or sequential inflation of the two balloons will result in a two-fold increase in the linear travel of the sliding head member.

V. Conclusion

The foregoing description of the various embodiments of the present invention has been presented for purposes of illustration and description. It is not intended to be exhaustive or to limit the invention to the precise form disclosed. Obvious modifications or variations are possible in light of the above teachings. The embodiments were chosen and described to provide the best illustration of the principles of the invention and its practical application to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally and equitably entitled. The drawings and preferred embodiments do not and are not intended to limit the ordinary meaning of the claims in their fair and broad interpretation in any way.

What is claimed is:

1. A joint manipulation device for manipulating the joint of a patient, said patient having two bones connected at said joint, said joint manipulation device comprising:
   A) an actuator comprising:
      1) a cylinder portion defining an interior cavity;
      2) a piston portion configured to move relative to said cylinder portion while within said interior cavity, said piston portion and said cylinder portion cooperating to at least partially define a subcavity within said interior cavity, said subcavity configured to expand as said piston portion moves in a direction within said interior cavity; and 3) an inflatable bladder member positioned at least partially inside said subcavity, said inflatable bladder member configured to, when being inflated, expand and to provide a pushing force relative to said piston portion causing said piston portion to move in said direction, thereby expanding said subcavity; and B) a linkage operatively coupled with said actuator and configured for operatively coupling with said joint of said patient, said linkage configured to be activated and, when operatively coupled with said joint of said patient, to flex said joint upon movement of said piston portion in said direction.

2. The joint manipulation device of claim 1, wherein said linkage is configured to be activated and, when operatively coupled with said joint of said patient, to transfer force from said piston portion sufficient to flex said patient joint.

3. The joint manipulation device of claim 2, wherein said linkage includes a flexible tension member configured to transmit said force through tension.

4. The joint manipulation device of claim 2, wherein said linkage includes a substantially rigid compression member configured to transmit said force through compression.

5. The joint manipulation device of claim 1, further comprising a patient connection and manipulation device operatively coupled with said patient and said linkage, wherein said patient connection and manipulation device is configured to flex said joint of said patient upon activation of said linkage.

6. The joint manipulation device of claim 5, wherein said linkage is configured to be activated and, when operatively coupled with said joint of said patient, to transfer force from said piston portion to said patient connection and manipulation device.

7. The joint manipulation device of claim 6, wherein said linkage includes a flexible tension member transferring said force through tension.

8. The joint manipulation device of claim 6, wherein said linkage includes a substantially rigid compression member transferring said force through compression.

9. A joint manipulation device for manipulating the joint of a patient, said patient having two bones connected at said joint, said joint manipulation device comprising:

A) an actuator itself comprising:
1) a cylinder portion defining an interior cavity;
2) a piston portion configured to move linearly relative to said cylinder portion while within said interior cavity, said piston portion and said cylinder portion cooperating to at least partially define a subcavity within said interior cavity, said subcavity configured to expand as said piston portion moves in a direction within said interior cavity; and
3) an inflatable bladder member positioned at least partially inside said subcavity, said inflatable bladder member configured to, when being inflated, expand and to provide a pushing force relative to said piston portion causing said piston portion to move in said direction, thereby expanding said subcavity; and B) a linkage operatively coupled with said actuator and configured for operatively coupling with said joint of said patient, said linkage configured to be activated and, when operatively coupled with said joint of said patient, to flex said joint upon movement of said piston portion in said direction.

10. The joint manipulation device of claim 9, wherein said linkage is configured to be activated and, when operatively coupled with said joint of said patient, to transfer force from said piston portion sufficient to flex said patient joint.

11. The joint manipulation device of claim 10, wherein said linkage includes a flexible tension member configured to transmit said force through tension.

12. The joint manipulation device of claim 11, wherein said flexible tension member has one end operatively coupled to said piston portion.

13. The joint manipulation device of claim 11, wherein said flexible tension member is configured to slide over said piston portion.

14. The joint manipulation device of claim 10, wherein said linkage includes a substantially rigid compression member configured to transmit said force through compression.

15. The joint manipulation device of claim 14, further comprising a patient connection and manipulation device operatively coupled with said patient and said linkage, wherein said patient connection and manipulation device is configured to flex said joint of said patient upon activation of said linkage.

16. The joint manipulation device of claim 15, wherein said linkage is configured to be activated and, when operatively coupled with said joint of said patient, to transfer force from said piston to said patient connection and manipulation device.

17. The joint manipulation device of claim 16, wherein said linkage includes a flexible tension member transferring said force through tension.

18. The joint manipulation device of claim 16, wherein said linkage includes a substantially rigid compression member transferring said force through compression.

19. The joint manipulation device of claim 9, wherein said inflatable bladder member is a first inflatable bladder member and further comprising a second inflatable bladder member also within said cavity and operating in conjunction with said first inflatable bladder member, said second inflatable bladder member being placed in between the first inflatable bladder member and the piston portion.

20. A joint manipulation device for manipulating the joint of a patient, said patient having two bones connected at said joint, said joint manipulation device comprising:

A) an actuator comprising:
1) a cylinder portion defining an interior cavity;
2) a piston portion configured to move linearly relative to said cylinder portion while within said interior cavity, said piston portion and said cylinder portion cooperating to at least partially define a subcavity within said interior cavity, said subcavity configured to expand as said piston portion moves within said interior cavity; and
3) an inflatable bladder member positioned at least partially inside said subcavity, said inflatable bladder member configured to, when being inflated, expand and to provide a pushing force relative to said piston portion causing said piston portion to move in said direction, thereby expanding said subcavity;

B) a linkage operatively coupled with said actuator and configured for operatively coupling with said joint of said patient, said linkage configured to be activated and, when operatively coupled with said joint of said patient, to flex said joint upon movement of said piston portion in said direction; and C) a patient connection and manipulation device operatively coupled with said patient and said linkage, wherein said patient connection and manipulation device is positioned intermediate said patient and said linkage, and wherein said patient connection and manipulation device is configured to at least partially assist flexion of said joint of said patient upon activation of said linkage.

21. The joint manipulation device of claim 20, wherein said linkage is configured to be activated and, when operatively coupled with said joint of said patient, to transfer force from said piston portion sufficient to flex said patient joint.

22. The joint manipulation device of claim 21, wherein said linkage includes a flexible tension member configured to transmit said force through tension.

23. The joint manipulation device of claim 22, wherein said flexible tension member has one end operatively coupled to said piston portion.

24. The joint manipulation device of claim 22, wherein said flexible tension member is configured to slide over said piston portion.

25. The joint manipulation device of claim 20, wherein said patient connection and manipulation device is configured to manipulate a joint in said patient's hand.

26. The joint manipulation device of claim 20, wherein said patient connection and manipulation device is configured to manipulate a joint in said patient's finger.

27. The joint manipulation device of claim 20, wherein said patient connection and manipulation device is configured to manipulate a joint in said patient's limb.

28. The joint manipulation device of claim 20, wherein said patient connection and manipulation device is configured to manipulate a joint in said patient's torso.

29. The joint manipulation device of claim 20, wherein said inflatable bladder member is a first inflatable bladder member and further comprising a second inflatable bladder member also within said cavity and operating in conjunction with said first inflatable bladder member, said second inflatable bladder member being placed in between the first inflatable bladder member and the piston portion.

30. A joint manipulation device for manipulating the joint of a patient, said patient having two bones connected at said-joint, said joint manipulation device comprising:
A) an actuator comprising:
1) a cylinder portion defining an interior cavity;
2) a piston portion configured to move relative to said cylinder portion while within said interior cavity; and
3) an inflatable bladder member positioned at least partially inside said interior cavity of said cylinder portion, said inflatable bladder member configured to, when being inflated, move relative to said cylinder portion, such that said piston portion moves relative to said cylinder portion in a direction away from said inflatable bladder member; and
B) a linkage operatively coupled with said actuator and configured for operatively coupling with said joint of said patient, said linkage configured to be activated and, when operatively coupled with said joint of said patient, to flex said joint upon inflation of said inflatable bladder member.

31. A joint manipulation device for manipulating the joint of a patient, said patient having two bones connected at said joint, said joint manipulation device comprising:
A) an actuator comprising:
1) a cylinder portion defining an interior cavity;
2) a piston portion configured to move relative to said cylinder portion while within said interior cavity; and
3) an inflatable bladder member positioned at least partially inside said interior cavity of said cylinder portion, said inflatable bladder member configured to, when being inflated, provide a pushing force relative to said piston portion to cause movement of said piston portion relative to said cylinder portion, said movement being in a direction away from said inflatable bladder member; and
B) a linkage operatively coupled with said actuator and configured for operatively coupling with said joint of said patient, said linkage configured to be activated and, when operatively coupled with said joint of said patient, to flex said joint upon inflation of said inflatable bladder member.

32. A joint manipulation device for manipulating the joint of a patient, said patient having two bones connected at said joint, said joint manipulation device comprising:
A) an actuator comprising:
1) a cylinder portion defining an interior cavity;
2) a piston portion configured to move relative to said cylinder portion while within said interior cavity; and
3) an inflatable bladder member positioned at least partially inside said interior cavity of said cylinder portion, said inflatable bladder member configured to, when being inflated, provide a pushing force, at an exterior surface of said inflatable bladder member, relative to said piston portion to cause movement of said piston portion relative to said cylinder portion, said movement being in a direction away from said inflatable bladder member; and
B) a linkage operatively coupled with said actuator and configured for operatively coupling with said joint of said patient, said linkage configured to be activated and, when operatively coupled with said joint of said patient, to flex said joint upon inflation of said inflatable bladder member.

33. A joint manipulation device for manipulating the joint of a patient, said patient having two bones connected at said joint, said joint manipulation device comprising:
(A) an actuator, said actuator itself comprising:
(1) a cylinder portion defining an interior cavity;
(2) a piston portion configured to move relative to said cylinder portion while within said interior cavity, said piston portion and said cylinder portion cooperating to at least partially define a subcavity within said interior cavity, said subcavity configured to expand as said piston portion moves in a direction within said interior cavity; and
(3) an inflatable bladder member positioned at least partially inside said subcavity, said actuator configured such that inflation of said inflatable bladder member causes said inflatable bladder member to expand and to provide a pushing force relative to said piston portion, such that said piston portion moves in said direction and said subcavity expands; and
(B) a linkage operatively coupled with said actuator and configured for operatively coupling with said joint of said patient, said linkage configured to be activated and, when operatively coupled with said joint of said patient, to flex said joint upon movement of said piston portion in said direction.

* * * * *